United States Patent [19]

Preti

[11] Patent Number: 4,467,814

[45] Date of Patent: Aug. 28, 1984

[54] METHOD FOR DETECTING BOVINE ESTRUS BY DETERMINING METHYL HEPTANOL CONCENTRATIONS IN VAGINAL SECRETIONS

[75] Inventor: George Preti, Philadelphia, Pa.

[73] Assignee: Monell Chemical Senses Center, Philadelphia, Pa.

[21] Appl. No.: 359,954

[22] Filed: Mar. 19, 1982

[51] Int. Cl.$^3$ ............................................. A61B 10/00
[52] U.S. Cl. ................................................... 128/738
[58] Field of Search ........................................ 128/738

[56] References Cited

U.S. PATENT DOCUMENTS 3,986,494 10/1976 Preti et al. ............................... 128/2
4,010,738 3/1977 Preti et al. ............................... 128/2
4,119,089 10/1978 Preti et al. ............................... 128/2

OTHER PUBLICATIONS

J. Ladewig and B. Hart "Demonstration of Estrus-Related in Cow Urine by Operant Conditioning of Rats", *Biology of Reproduction* 24:1165–1169 (1981).

G. Preti & G. Huggins, "Cyclical Changes in Volatile Acidic Metabolites of Human Vaginal Secretions and Their Relation to Ovulation", *Journal of Chemical Ecology*, vol. 1, No. 3, pp. 361–376 (Jul., 1975).

G. Huggins & G. Preti, "Volatile Constituents of Human Vaginal Secretions", *American Journal of Obstetrics and Gynecology*, vol. 126, No. 1, pp. 129–136 (Sep. 1, 1976).

G. Preti, R. C. Murphy & K. Biemann, "The Search for Organic Compounds in Various Apollo 12 Samples by Mass Spectrometry", *Proceedings of the Second Lunar Science Conference*, vol. 2, pp. 1879–1889, The M.I.T. Press, (1971).

S. D. Sastry, K. Buck, J. Janak, M. Dressler & G. Preti, "Volatiles Emitted by Humans", *Supplementary Volume to Biochemical Applications of Mass Spectrometry*, ed. by G. K. Waller, Chap. 34, p. 1086 (1980).

J. Kostelc, G. Preti, P. Zelson, N. H. Stoller & J. Tonzetich, "Salivary Volatiles as Indicators of Periodontitis", *Journal of Periodontal Research* 15:185–192 (1980).

A. Zlatkis, R. Brazell & C. Poole, "The Role of Organic Volatile Profiles in Clinical Diagnosis", *Clinical Chemistry*, vol. 27, No. 6, pp. 789–797 (1981).

J. Watson, & K. Biemann, "Direct Recording of High Resolution Mass Spectra of Gas Chromatographic Effluents", *Analytical Chemistry*, vol. 37, No. 7, pp. 844–851 (Jun., 1965).

H. Van Den Dool & P. Dec. Kratz, "A Generalization of the Retention Index System Including Linear Temperature Programmed Gas–Liquid Partition Chromatography", *Journal of Chromatography*, vol. 11, pp. 463–471 (1963).

D. R. Melrose, H. C. B. Reed & R. L. S. Patterson, "Androgen Steroids Associated with Boar Odor as an Aid to the Detection of Oestrus in Pig Artificial Insemination", *British Veterinary Journal*, vol. 127, pp. 497–501 (1971).

G. Preti, A. Smith, III, & G. Beauchamp, "Chemical and Behavioral Complexity in Mammalian Chemical Communication Systems: Guinea Pigs (*Cavia porcellus*), Marmosets (*Saguinus fuscicollis*) and Humans (*Homo sapiens*)", Chem. Signals in Vert. pp. 95–114, (1977).

M. Goodwin, K. M. Gooding, & F. Regnier "Sex Pheromone in the Dog", *Science*, vol. 203, No. 4380, pp. 559–561 (Feb. 9, 1979).

J. C. Price and D. J. Manning, "Changes in the Concentration of Volatiles in Cow Urine During Oestrus", *Proc. Int. Dairy Congress*, p. 1096 (1978).

C. A. Kiddy, D. S. Mitchell, D. J. Bolt, & H. W. Hawk, "Detection of Estrus-Related Odors in Cows by Trained Dogs", *Biology of Reproduction*, vol. 19, No. 2, pp. 389–395, (1978).

C. A. Kiddy & D. Mitchell, "Estrus-Related Odors in Cows: Time of Occurrence", *Journal of Dairy Science*, 64:267–271 (Feb., 1981).

J. G. Manns and H. D. Hafs, "Controlled Breeding in Cattle: A Review", *Can. J. Anim. Sci.* 56:121–130 (Jun. 1976).

J. F. Hurnik, G. J. King and H. A. Robertson, "Estrous and Related Behaviour in Postpartum Holstein Cows", *Applied Animal Ethology*, 2:55–68 (1975).

C. Kiddy "Variation in Physical Activity as an Indication of Estrus in Dairy Cows", *Journal of Dairy Science*, vol. 60, No. 2, pp. 235–243 (1977).

P. Gartland, J. Schiavo, C. E. Hall, R. H. Fote and N. R. Scott, "Detection of Estrus in Dairy Cows by Electrical Measurements of Vaginal Mucus and by Milk Progesterone", *Journal of Dairy Science,* 59:982–985 (1976).

H. H. Sambras & G. H. Waring, "Effects of Urine from Estrous Cows in Libido in Bulls", *Z. Savgetierkd,* 40:49 (1975).

A. M. Paleologou, "Detecting Oestrus in Cows by a Method Based on Bovine Sex Pheromones", *The Veterinary Record,* vol. 100, No. 15, p. 319 (Apr. 9, 1977).

Epple, 1982.

J. Tonzetich & S. K. Ng, "Reduction of Malodor by Oral Clensing Procedures", *Oral Surgery,* vol. 42, No. 2, pp. 172–181, (Jul.-Dec., 1976).

G. Ohloff & I. Flament, "The Role of Heteroatomic Substances in the Aroma Compounds of Foodstuffs", *Fortschritte der Chemie Organischer Naturstoffe,* vol. 36, pp. 231–253 (1978).

Y. Katz, L. Dashow & A. Epple, "Circulating Steroid Hormones of Anadromous Sea Lampreys under Various Experimental Conditions", *General and Comparative Endocrinology* 48:261–268 (1982).

J. P. Signoret, "Chemical Communication and Reproduction in Domestic Mammals", *Mammalian Olfaction, Reproductive Processes, and Behavior,* Chapter 12 pp. 243–256 Academic Press 1976.

G. Preti & G. R. Huggins, "Organic Constituents of Vaginal Secretions", *The Human Vagina,* Chapter 10, North Holland Publishing Co., pp. 151–166 (1978).

J. Tonzetich, "Oral Malodour: An Indicator of Health Status and Oral Cleanliness", *International Dental Journal,* vol. 28, No. 3, pp. 309–319 (Sep. 1978).

G. Preti, P. Zelson, J. Kostelc, G. Huggins & J. Tonzetich, "Cyclical Variations in Salivary Volatiles", *Journal of Dental Research,* 59:356 (Special Issue A), 1980.

G. Preti, G. Huggins, G. Silverberg, "Alterations in the Organic Compounds of Vaginal Secretions Caused by Sexual Arousal", *Fertility and Sterility,* vol. 32, No. 1, pp. 47–54 (Jul. 1979).

G. Huggins, & G. Preti, "Vaginal Odors and Secretions", *Clinical Obstetrics and Gynocology,* vol. 24, No. 2, pp. 355–377 (Jun. 1981).

*Primary Examiner*—Benjamin R. Padgett
*Assistant Examiner*—T. J. Wallen
*Attorney, Agent, or Firm*—Woodcock Washburn Kurtz Mackiewicz & Norris

[57]   ABSTRACT

A novel method for determining when cows are in estrus is disclosed comprising the step of monitoring the vaginal secretions of a cow to determine an increase in the amount of an indicator compound in said secretions. A significant increase in the amount of the indicator compound, concentrations above about 0.1 micrograms per gram of collected secretion, is indicative of estrus. The preferred indicator alcohols have ethyl ester indices of 8.1 to 8.9. In particular these alcohols are methyl-1-heptanols, such as 6-methyl-1-heptanol, or are methyl hydroxy heptenes, such as 2-methyl-7 hyroxy-$\Delta$-3-4 heptene. Alternatively, a cow may be determined to be in estrus simply to ascertaining that the concentration of methyl-1-heptanol is at least 0.1 microgram per gram of collected vaginal secretion.

16 Claims, 18 Drawing Figures

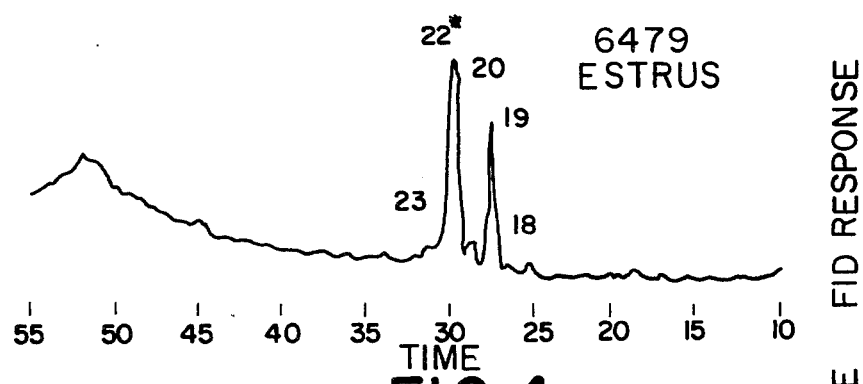
FIG. 4
FIG. 4a
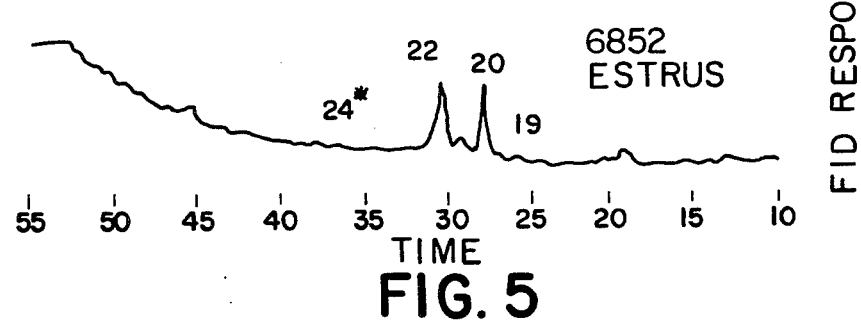
FIG. 5
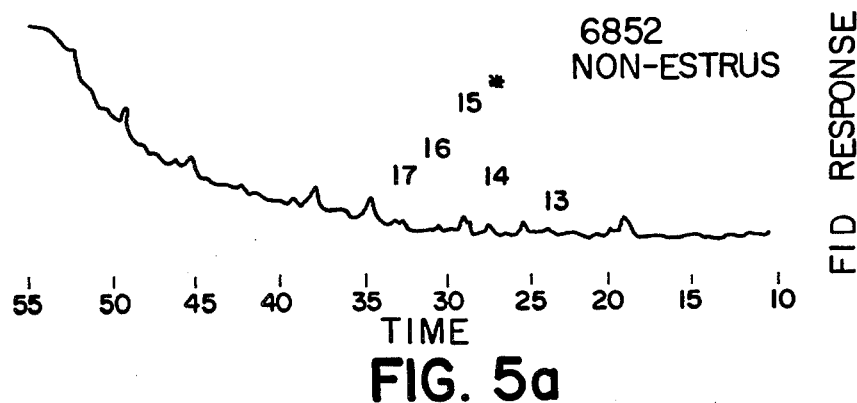
FIG. 5a

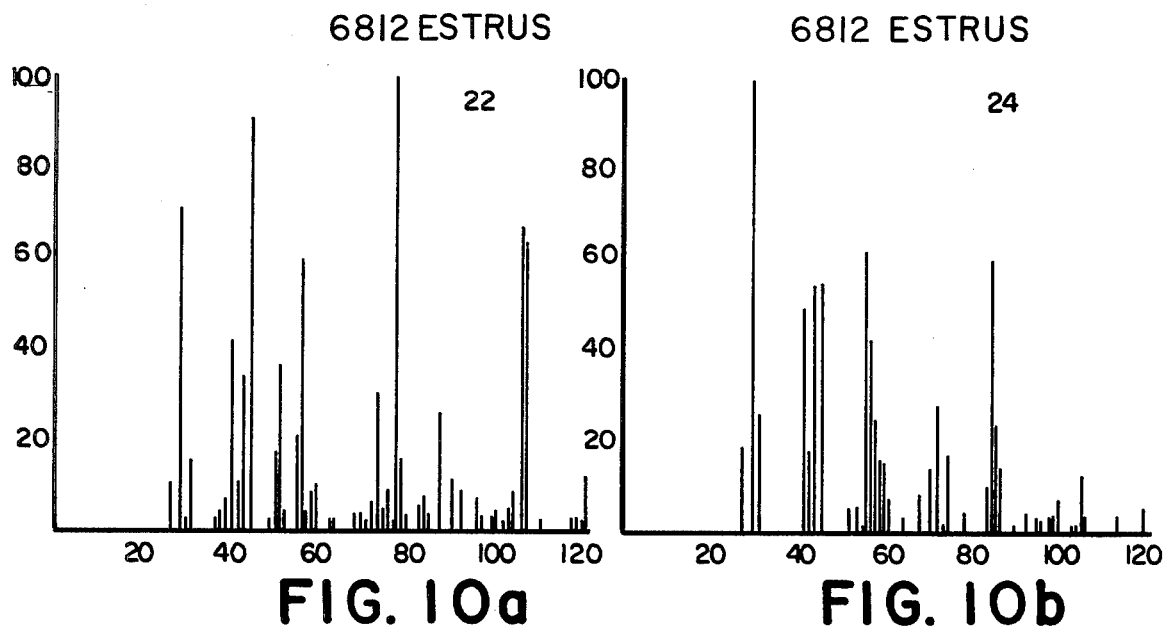
FIG. 10a
FIG. 10b
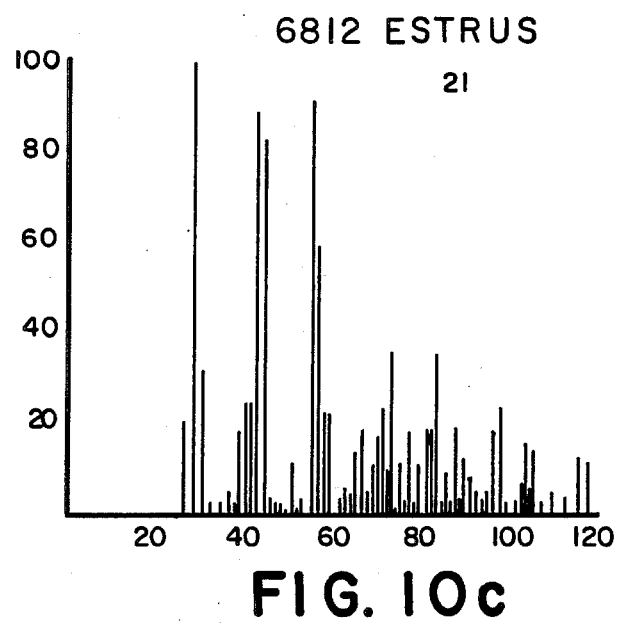
FIG. 10c

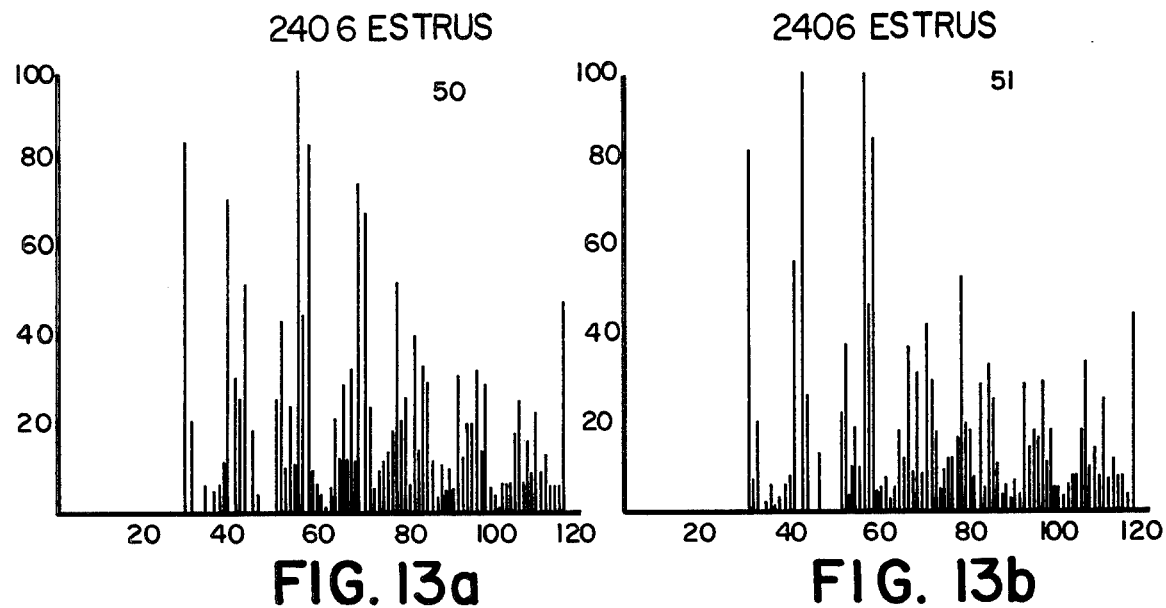
FIG. 13a
FIG. 13b
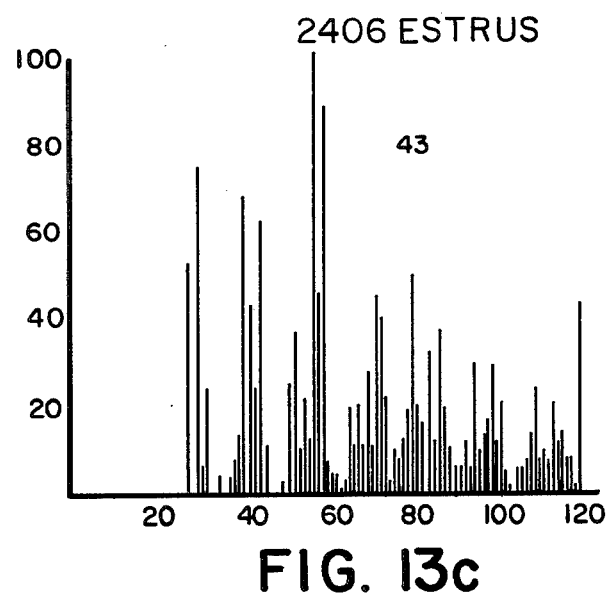
FIG. 13c

COW 6808 ESTRUS A

| Compound | Molecular Wt. and Formula | Similarity Index |
|---|---|---|
| 1-HEPTANOL, 6-METHYL- | 130 C8H18O | 0.660 |
| 1-DECENE, 8-METHYL- | 154 C11H22 | 0.592 |
| 4-UNDECANOL, 7-ETHYL-2-METHYL | 214 C14H30O | 0.557 |
| 2-UNDECENE, 4,5-DIMETHYL-, R*,R*'-(E)- | 182 C13H26 | 0.528 |
| 2-DODECENAL | 182 C12H22O | 0.522 |
| 1-TRIDECENE | 182 C13H26 | 0.509 |
| 1,2-CYCLOPENTANEDIOL, 3-METHYL- | 116 C6H12O2 | 0.503 |
| 1-HEXENE, 3,5,5-TRIMETHYL- | 126 C9H18 | 0.497 |
| 1-TETRADECENE | 196 C14H28 | 0.489 |
| DECANE, 1-(ETHENYLOXY)- | 184 C12H24O | 0.487 |

FIG. 16

COW 6806 ESTRUS B

| Compound | Molecular Wt and Formula | Similarity Index |
|---|---|---|
| 1,3-CYCLOPENTANEDIOL, CIS- | 102 C5H10O2 | 0.522 |
| 1-HEPTANOL,6-METHYL- | 130 C8H18O | 0.513 |
| 1,3-CYCLOPENTANEDIOL,TRANS- | 102 C5H10O2 | 0.488 |
| 1-HEPTANOL,2,4-DIMETHYL-,(R,R)-(+)- | 144 C9H20O | 0.452 |
| 1-HEPTANOL,2,4-DIMETHYL-,(2S,4R)-(-)- | 144 C9H20O | 0.449 |
| ACETIC ACID, 2-ETHYLHEXYL ESTER | 172 C10H20O2 | 0.444 |
| 1-HEXENE, 5,5-DIMETHYL- | 112 C8H16 | 0.438 |
| 4-UNDECANOL, 7-ETHYL-2-METHYL- | 214 C14H30O | 0.411 |
| ISOOCTANE, (ETHENYLOXY)- | 156 C10H20O | 0.409 |
| 1-DECENE,2,4-DIMETHYL- | 168 C12H24 | 0.401 |

FIG. 17

COW 6808 ESTRUS C

| Compound | Molecular Wt and Formula | Similarity Index |
|---|---|---|
| ISOOCTANOL | 130 C8H18O | 0.708 |
| 1-OCTANOL | 130 C8H18O | 0.656 |
| 1-HEPTENE,6-METHYL- | 112 C8H16 | 0.611 |
| 3-UNDECENE, (2)- | 154 C11H22 | 0.609 |
| CYCLOPROPANE,1,2-DIMETHYL-1-PENTYL | 140 C10H20 | 0.590 |
| 3-UNDECENE, (E)- | 154 C11H22 | 0.583 |
| 1-HEXANOL,5-METHYL | 116 C7H16O | 0.581 |
| ACETIC ACID,TRIFLOURO-,OCTYL ESTER | 226 C10H17F3O2 | 0.580 |
| 1-HEXANOL,3-METHYL- | 116 C7H16 | 0.576 |
| 1-OCTENE | 112 C8H16 | 0.575 |

METHOD FOR DETECTING BOVINE ESTRUS BY DETERMINING METHYL HEPTANOL CONCENTRATIONS IN VAGINAL SECRETIONS

BACKGROUND OF THE INVENTION

The present invention relates to methods for determining bovine estrus, and more particularly to chemical techniques for ascertaining when artificial insemination is likely to produce offspring.

In order to increase milk production and maximize offspring in both dairy and beef cattle, detection of estrus and the use of artificial insemination are important to proper herd management. Detection of estrus has become more acute with increased dairy herd size, escalating labor costs, use of artificial insemination in beef herds, and with the use of loose housing systems for dairy cattle. Identification of one or more metabolites in a readily accessible body fluid would be an important step in detecting bovine estrus.

The importance of estrus detection in bovines, where reproduction is primarily based on artificial insemination, is well established (Manns and Hafs, 1976). This has led to a variety of attempts to establish a simple method to determine this important state. These have included studying cow mounting behavior in free ranging situations (Hurnik et al., 1975), the amount of movement displayed during the estrous cycle (as measured by a pedometer) (Kiddy, 1977) and measurement of electrical resistance of vaginal mucus (Gartland et al., 1976).

Sambras and Waring (1975) documented the ability of sexually experienced bulls to discriminate estrous females from non-estrous ones on the basis of urinary odors. In addition, Paleologou (1977) found that vaginal mucus from estrous cows would stimulate bulls to mount dummies used for semen collection. Mucus from non-estrous cows had no effect. Studies such as these suggest that bulls may base part of their discrimination between estrous and non-estrous cows on odors found in the genital region of female bovine. Consequently, while the role of behaviorally important odors from estrous cows in attracting bulls has not been definitely established, there is evidence for the existence of such odors.

An effort to document the types of compounds present in cow urine which might change during the estrous cycle was reported by Price and Manning (1978). Using a headspace concentration technique in combination with GC/MS, the concentration change in approximately 30 volatile compounds on a daily basis across 3 menstrual cycles from 1 non-lactating cow was examined. No reproducible changes were seen in the concentration of these volatiles, even though the cow displayed good estrous behavior.

Studies by Kiddy et al (1978, 1981) employing trained dogs, show that these animals can differentiate odors from a variety of bovine body fluids (blood, milk, urine, vaginal secretions) obtained from estrous and non-estrous cows. Hence, a quantitative and/or qualitative change in the volatiles from readily available sources were thought to be characteristic of estrus. Another recent investigation by Ladewig and Hart (1981) found that rats could be trained to detect estrous-related odors in cow urine. It is not surprising that the rats used in this study were able to find a difference in the urinary odor while instrumental methods were not, since mammalian olfactory abilities often exceed the instrumental sensitivity of a GC/MS used in the normal scanning mode.

Each of these studies demonstrate that there is a characteristic change in excreted metabolites due to a change in hormonal state. However, it is not known if the dogs and rats are employing the same odors that bulls employ.

Some success has been achieved at predicting and determining ovulation in other species, particularly humans. Please refer to the disclosures of U.S. Pat. Nos. 3,986,494, 4,010,738 and 4,119,089. While the techniques of these disclosures are described as being applicable to livestock such as cows, the art has yet to identify or suggest the particular compositions disclosed herein as being useful in analytical technique to determine when a cow is in estrus.

SUMMARY OF THE INVENTION

The present invention provides a novel method for determining bovine estrus comprising the step of monitoring cow vaginal secretions over time to determine a significant increase in the amounts of an indicator compound in said secretions, said increase in the amounts of said indicator compound being indicative of estrus. In the preferred embodiment, said compound elutes on a gas chromatograph to have an ethyl ester index of between 8.1 and 8.9, and increases from a concentration of less than 0.001 micrograms per gram of secretion to greater than 0.1 microgram per gram of secretion. Indicator compounds for use in the method of the present invention include such alcohols having 8 carbon atoms. The preferred indicator alcohols are methyl-1-heptanols, particularly 6-methyl-1-heptanol. It is also within the scope of the present invention to detect unsaturated $C_8$ alcohols.

The present invention also provides a novel method for determining when a cow is in estrus comprising the step of determining the methyl-1-heptanol concentration in the vaginal secretions of said cow, a concentration of at least 0.1 microgram per gram of said methyl-1-heptanol being indicative of estrus. For most estrous cows, the concentrations of methyl heptanol, particularly 6-methyl-1-heptanol, is between about 0.16 to 0.83 micrograms per gram of vaginal secretion. By way of comparison, the concentration of 6-methyl-1-heptanol in the vaginal secretions of non-estrous cows is far less than 0.01 micrograms per gram of vaginal secretion.

Accordingly, a primary object of the present invention is the provision of an improved method for detecting bovine estrus.

A further object of the present invention is the provision of a method for detecting bovine estrus by detecting the concentration of an indicator compound in the vaginal secretions of a test cow.

A further object of the present invention is the provision of a method for increasing bovine fertility and/milk production by identifying cows ready for artificial insemination.

These, and other objects of the present invention, will become apparent from the following, more detailed description.

BRIEF DESCRIPTION OF THE DRAWINGS

FIGS. 1–7 are gas chromatographic profiles obtained on a combining bas chromatograph—mass spectrometer of estrous and non-estrous samples collected from cows no. 2443, 6806, 6812, 6479, 6852, 6479, and 6852, respectively;

FIGS. 8–14 are normalized mass spectra of several of the components from each of the estrous samples of FIG. 1–7; the numeral located below the cow identification number of each spectra corresponds to its scan number as indicated on the corresponding chromatographic profiles of FIGS. 1–7;

FIGS. 16, 17 and 18 are charts of compounds indicating a similarity to the 4 mass spectra shown in FIG. 9 (taken from cow no. 6806), which charts were generated by a computer search of the 31,600 mass spectra at the MIT Mass Spectrometry Laboratory.

DESCRIPTION OF THE PREFERRED EMBODIMENTS

Figure 1:
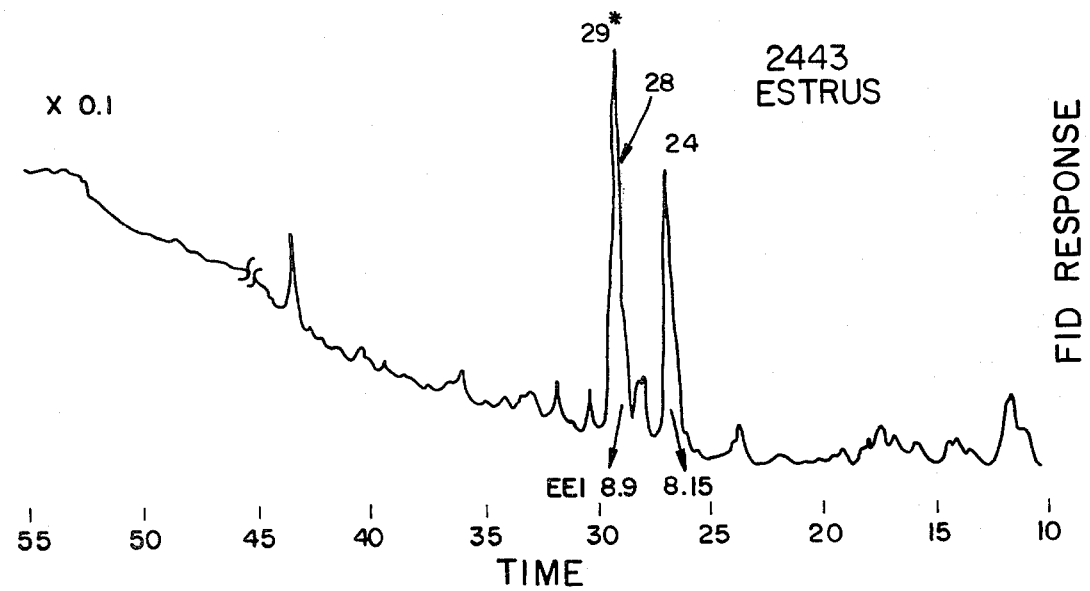
Figure 1A:
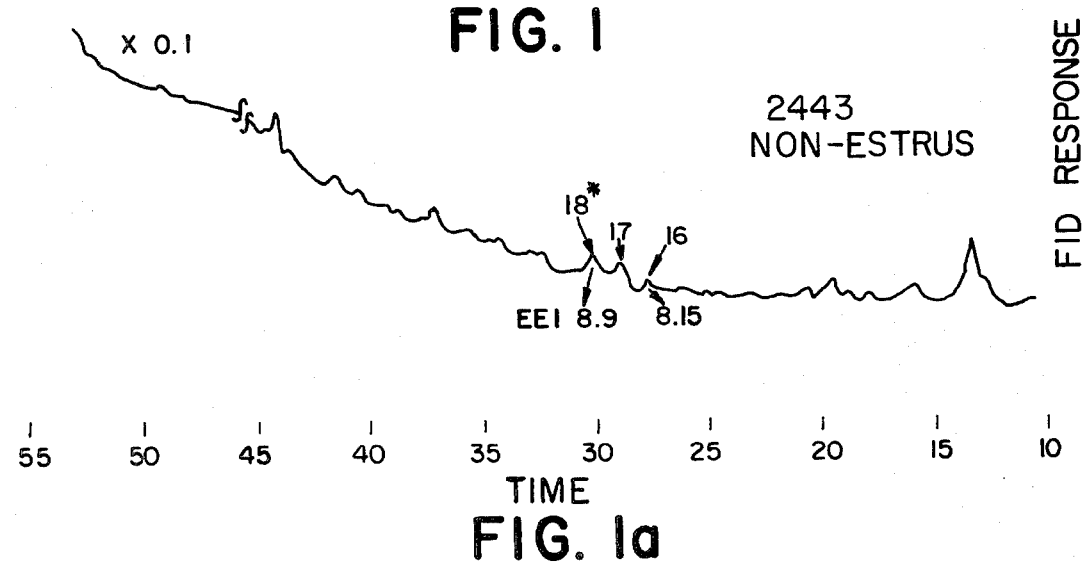

While various examples are described hereinafter for the purposes of illustration, those of ordinary skill in this art will recognize that various departures from the materials and methods described herein can be made without departing from the scope of the present invention, which is defined more particularly in the appended claims.

The following procedures were used to collect, prepare and analyse vaginal secretions in accordance with the preferred method of the present invention.

Vaginal fluids were supplied by Drs. Charles Kiddy and Harold Hawk. Commercially available tampons (Tampax) were used for collection of vaginal fluids. These were precleaned in the laboratory using previously documented techniques (Preti and Huggins, 1975, Huggins and Preti, 1976). After extraction, drying and weighing, the tampons were returned to their original holders and stored in clean glass bottles. Jars for holding the tampons after secretion collection were all precleaned in our laboratories. The cleaning procedures employed were similar to those used for cleaning glassware used in the analyses of lunar samples (Preti et al., 1971).

Vaginal secretions were collected by placing them near the animal's cervix. Although several different collection times were initially employed (ranging from 15 min to 1 hr), the majority of the tampons were left in place for 1 hr. After collection, samples of vaginal fluids were frozen at $-20°$ C. until shipment to the Monell Center packed in dry ice. Here they were frozen at $-60°$ C. until ready for analysis.

Several different analytical schemes were tried in order to discern differences between estrous and non-esterous samples. Before analysis of vaginal fluids, the samples were thawed. In the case of tampons, these were weighed to obtain the secretion weight prior to any analytical procedures.

For analysis, the tampons were placed in a 2-necked round-bottom flask. Each sample (tampon) was held at $39° \pm 1°$ C. during collection of volatiles. With each sample, the round-bottom flask was sealed with Teflon joints through which passed a nitrogen line and a collection tube. Volatiles were collected using a variety of nitrogen flow rates to test various collection parameters. A flow of 60 ml/min was employed in a majority of the samples in the results discussed below.

Volatiles were swept out of the flask and through the collection tube consisting of a $6'' \times \frac{1}{8}''$ (O.D.) stainless steel tube filled with ~100 mg of Tenax (a 2,6-diphenyl-p-phenylene oxide polymer, Applied Science Labs., State College, PA). This polymer adsorbs organic compounds but retains little water and effectively concentrates organic compounds from aqueous sources (see Sastry et al., 1980; Kostelc et al., 1980 and Zlatkis et al., 1981 for reviews of the use of this technique).

Two, 2 hr collections were generally made from each of the vaginal headspace samples. These samples were stored in the Tenax tubes at $-60°$ C. until needed for analysis by gas chromatography (GC) or combined gas chromatography/mass spectrometry.

The GC/MS system used for compound identification consists of a Perkin-Elmer 990 GC interfaced to a Hitachi RMU-6L mass spectrometer via a Watson-Biemann separator (Watson and Biemann, 1965). Identification of all compounds were confirmed by comparison of mass spectra and chromatographic retention times with those from either commercially available or synthetically produced samples. Relative retention times on Carbowax were obtained by coinjection of headspace mixtures, extracts or authentic samples with a series of $C_2$–$C_{18}$ fatty acids ethyl esters to obtain their "ethyl ester index" (van den Dool and Kratz, 1963). A homologous series of $C_9$–$C_{36}$ hydrocarbons were used to obtain relative retention times of silanated derivatives.

For all mass spectra obtained in this study, the ionizing electron beam was 70 eV and the chamber temperature was kept at 200° C. A scan speed of 6 seconds for the mass range of m/z 5 to m/z 350 was employed.

A $12' \times 2$ mm (i.d.) glass 10% Carbowax 20M column with a 40 l/min He carrier gas flow was used in the routine analysis of headspace samples. The temperature program protocol used in the analyses was as follows: 50° C. for 8 min.; 50°–230° at 4°/min., 230° for 30 min. Organic materials collection on the Tenax were desorbed from the polymer and onto the front 6–8 in. of the Carbowax column which was cooled using crushed dry ice. The Tenax was rapidly heated to 240° C. for 15 min while its contents were swept by means of the carrier gas (He) onto the column. After desorption was complete, the dry ice was removed, the Tenax tube removed for the GC injector, the flow rate resumed through the GC column and the components separated on the column following the programmed temperature conditions cited above. This analysis is currently being adapted to 80–100 m $\times$ 1.0 mm capillary columns. These columns have from 1000–2000 theoretical plates/meter and are preferred for future research.

Using the above identified procedures, the following results were obtained:

1. Secretion Weight

Nineteen of the 29 paired estrous ("E") and non-estrous ("NE") tampons were worn for 1 hr. A paired t-test was used to give a measure of the difference in secretion weight during the 2 stages of the estrous cycle: secretion weight during estrous = $6.028$ gm $\pm 3.004$ (S.D.); secretion weight during non-estrous = $0.899$ gm $\pm 0.747$ (S.D.); $t = 7.485$, $p < 0.001$. The range seen in secretion weight was 0.489 gm to 11.253 gm for estrous samples and 0.001 gm to 3.083 gm for non-estrous samples.

2. Headspace Collections on Tenax—Vaginal Secretions

Volatiles present in the headspace above nine paired estrous (E) and non-estrous (NE) samples were individually collected on Tenax. Two, 2 hr collections were done in each case. The volatiles present in the second 2 hr samples were qualitatively identical to those in the first 2 hr collections; however, the first collections always contained larger amounts of constituents. The data from two of these animals is excluded from the discussion below for the following reasons: one animal (6630) was used in the initial experiment using Tenax when procedures were still being developed; and one animal (6686) showed a series of constituents never again seen in another animal superimposed on the constituents seen in the other animals. Consequently, this animal may have had some sort of vaginal anomaly which caused the appearance of these constituents. The compounds seen in these samples are shown in Table I:

TABLE I

Headspace Volatiles from Bovine Vaginal Fluids ≠

| Ethyl Ester Index (EEI) | Compound | Characteristic Ions in M.S.* m/z |
|---|---|---|
| | Methylene chloride | 86,84 |
| | Unknown | 31,43,45,59 |
| 4.14 | Toluene | 91,92 |
| 5.10 | Xylene | 106,105, 91 |
| | Aromatic hydrocarbons | 120,105,119,105 |
| 6.3 | Styrene | 104,103,78,77 |
| 6.7 | Hydroxy-propanone | 31,43,74 |
| 7.5 | Unknown | 31,57,73 |
| 8.15 | $C_8$ alcohols** | 97,84,83,70,69, 57,55,43,31, 57,55,43,41,31 |
| 8.70 | n-$C_{15}$ hydrocarbon | M+ 212 |
| 8.90 | $C_8$ alcohols** | 97,84,83,70,69 57,55,43,41,31, 98,69,68,57,55, 43-41 |
| 8.95 | Benzaldehyde | 106,105,77 |
| 9.71 | n-$C_{16}$ hydrocarbon | M+ 226 |
| 9.9 | gamma-hydroxy-butyric acid lactone | 86,85,56,42,41,29 |
| 10.17 | Furfuryl alcohol | 98,97,81,39 |
| 10.50 | Unknown | 126,111,109,83,55 |
| 10.7 | Unknown | 98,69 |
| | n-$C_{17}$ hydrocarbon | M+ 240 |
| 11.15 | Napthalene | M+ 128 |
| 11.5 | Unknown | 152,121,120, 92,93 |
| 11.7 | n-$C_{18}$ hydrocarbon | M+ 254 |
| | hydroxy-methyl-cyclopentenone | 112,97,69,55 |
| 12.1 | Methylnapthalene | 142,141 |
| | Unknown | 99,71,70,30 |
| 13.00 | Dodecanol | 168,140,125,112 82,81,55,41,31 |
| 13.28 | Phenol | 94,66,65 |
| 14.11 | p-Cresol | 108,107 |
| 15.05 | p-Ethyl phenol | 122,107 |
| | Antioxidant (?) | 236,221,143, 253,268 |

Figure 2:
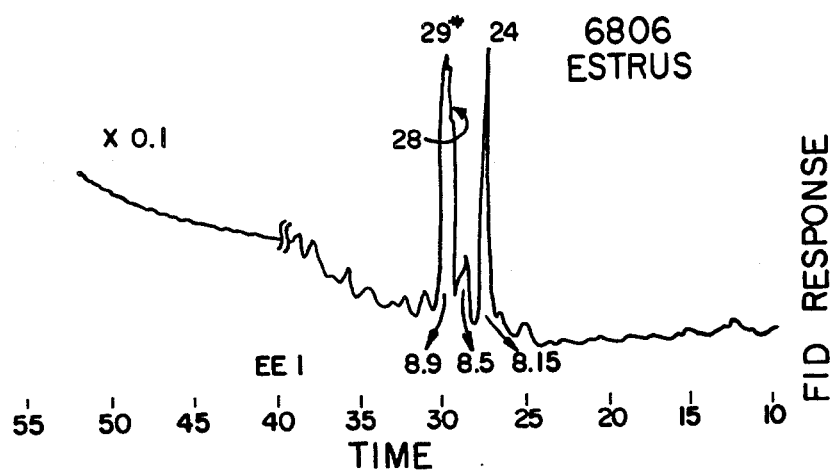
Figure 2A:
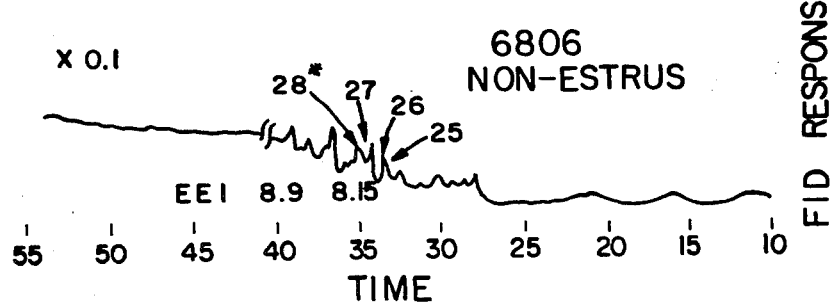
Figure 3:
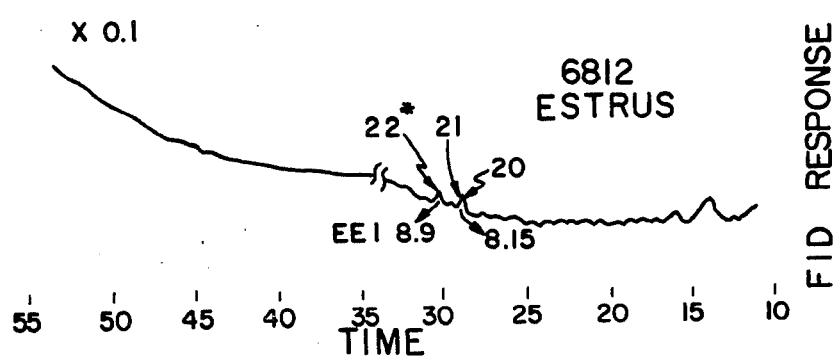
Figure 3A:
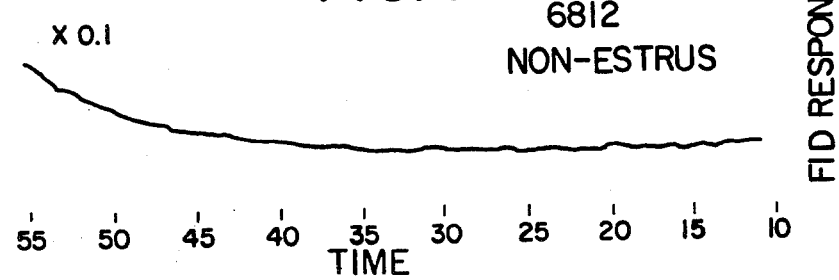
Figure 6:
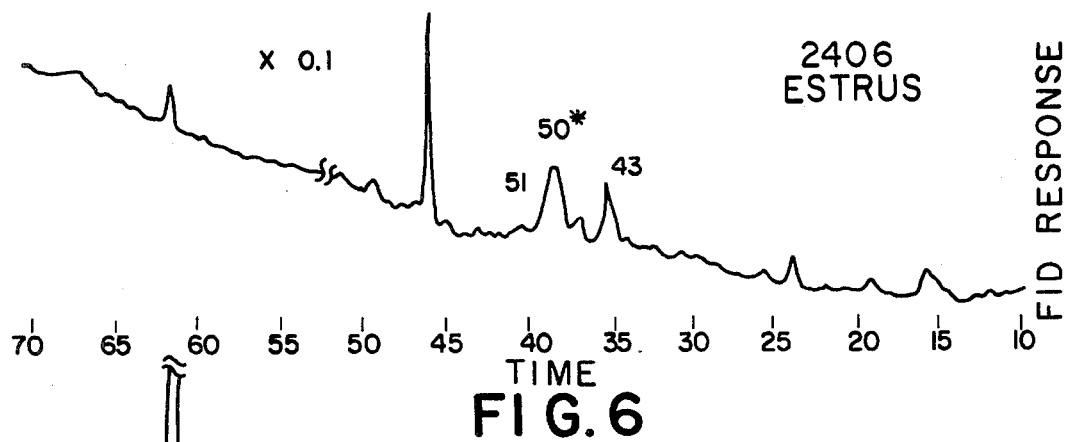
Figure 6A:
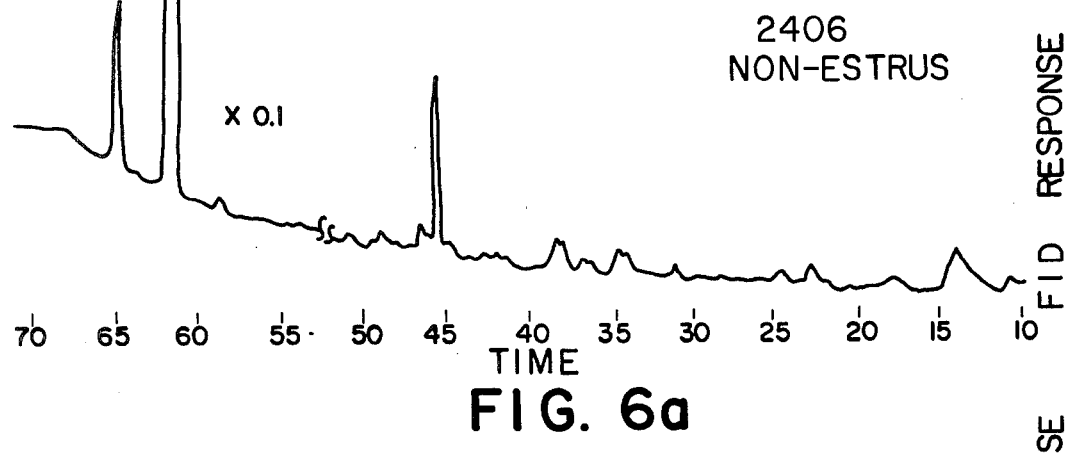
Figure 7:
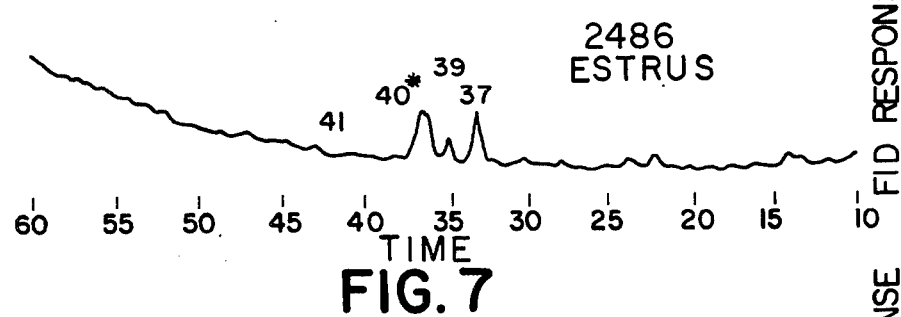
Figure 7A:
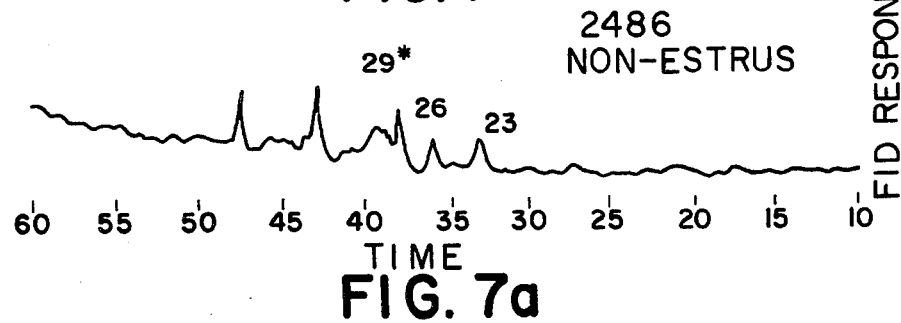

≠ 8 Estrous and 8 Non-Estrous samples
*Most intense ion(s) underlined
**Found in estrous samples In the seven E and NE samples, a distinct difference was seen in the volatiles. The profiles of constituents collected during the first 2 hr collection from these seven samples may be seen in FIGS. 1-7. The estrous samples show a series of peaks (labelled with scan numbers for identification) eluting between the times 25-35 min in cows 6812, 2443, 6806, 6852, and 6479 as well as between the times 30-40 min in cows 2406 and 2486. The latter two samples were run in a different Carbowax column from the other 5, which accounts for the different elution times of these constituents.

Figures 8A, 8B:
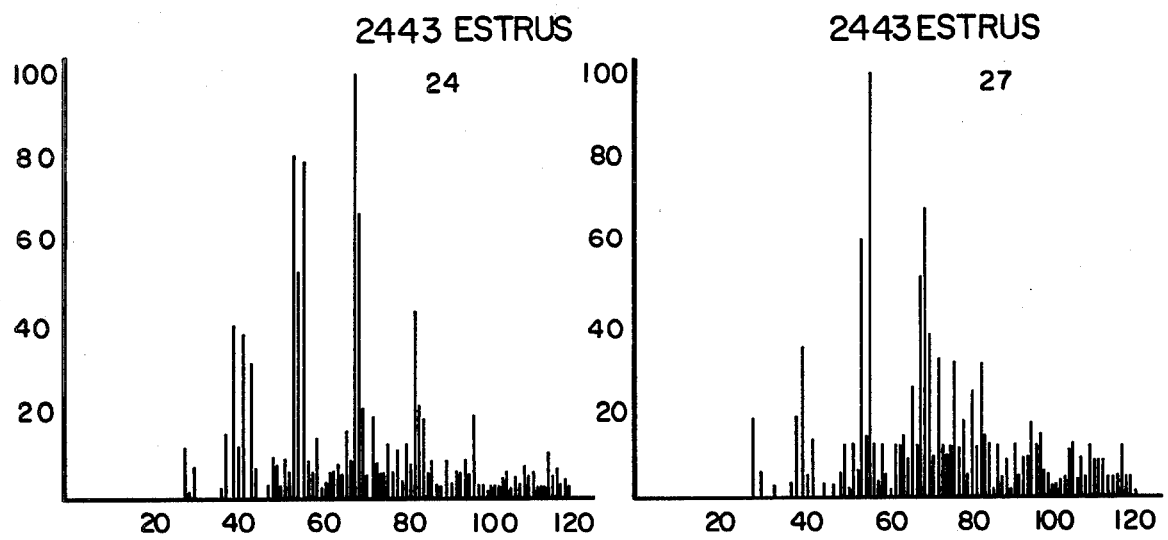
Figures 8C, 8D:
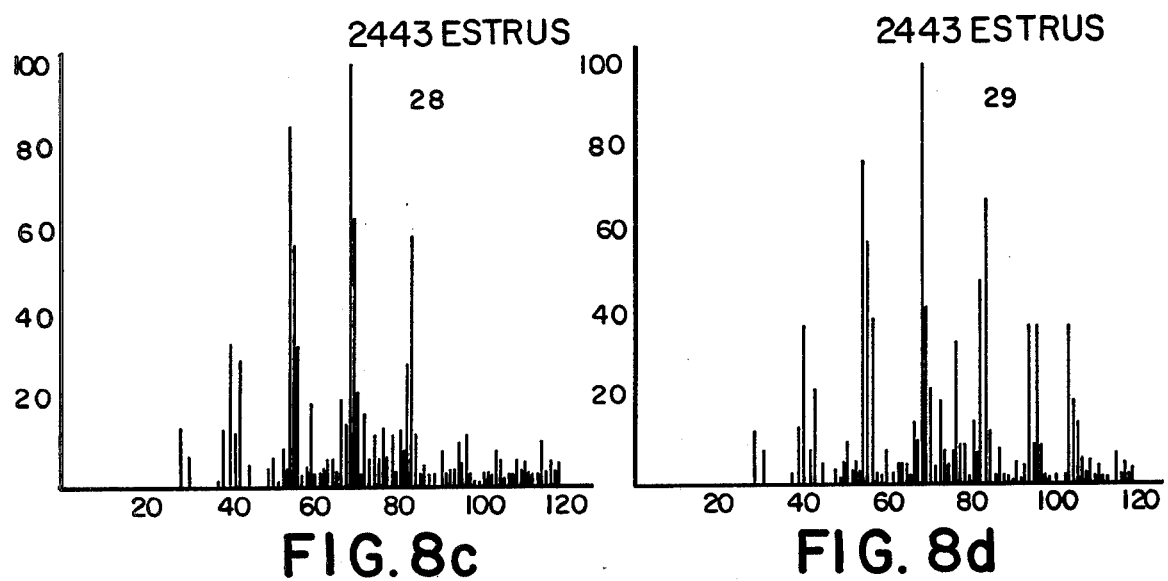
Figure 9A:
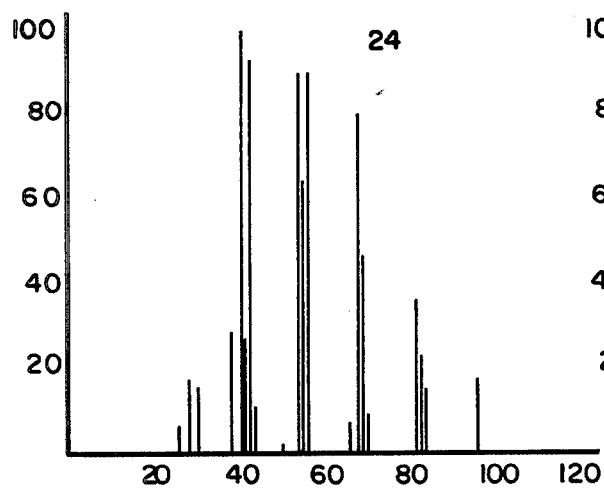
Figure 9B:
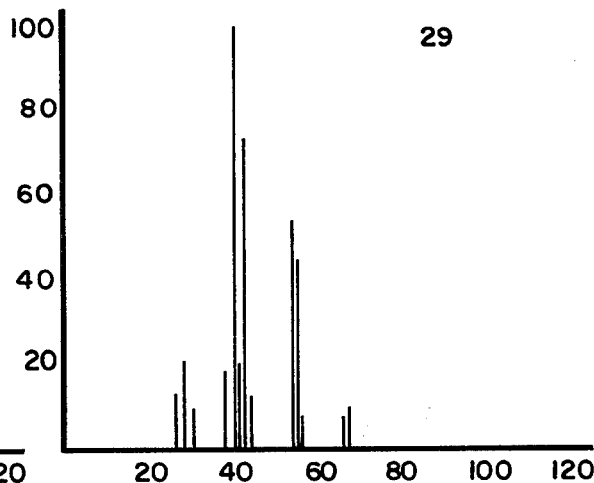
Figure 9C:
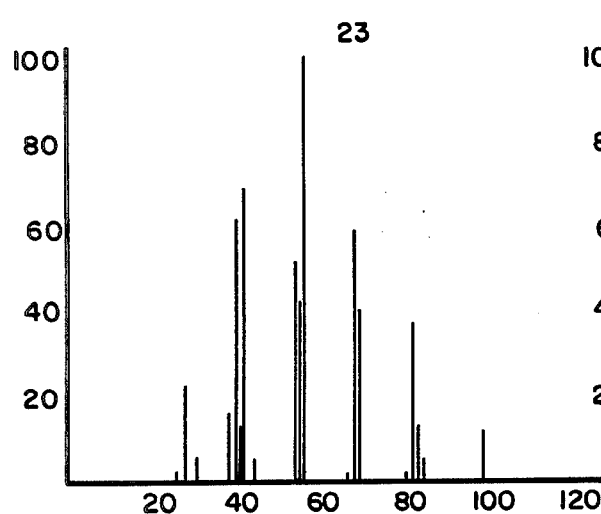
Figure 9D:
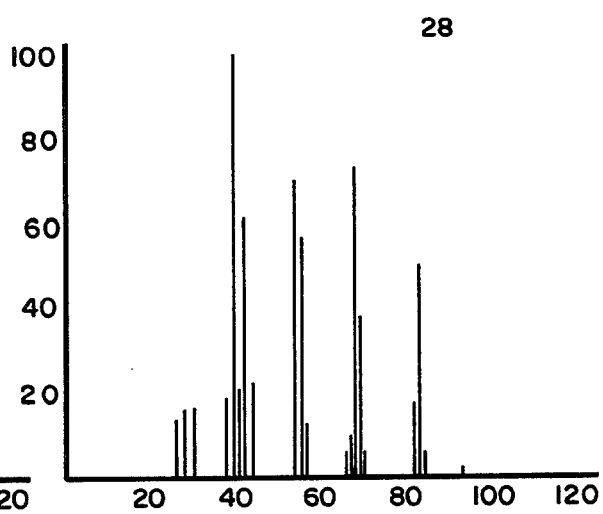
Figures 11A, 11B:
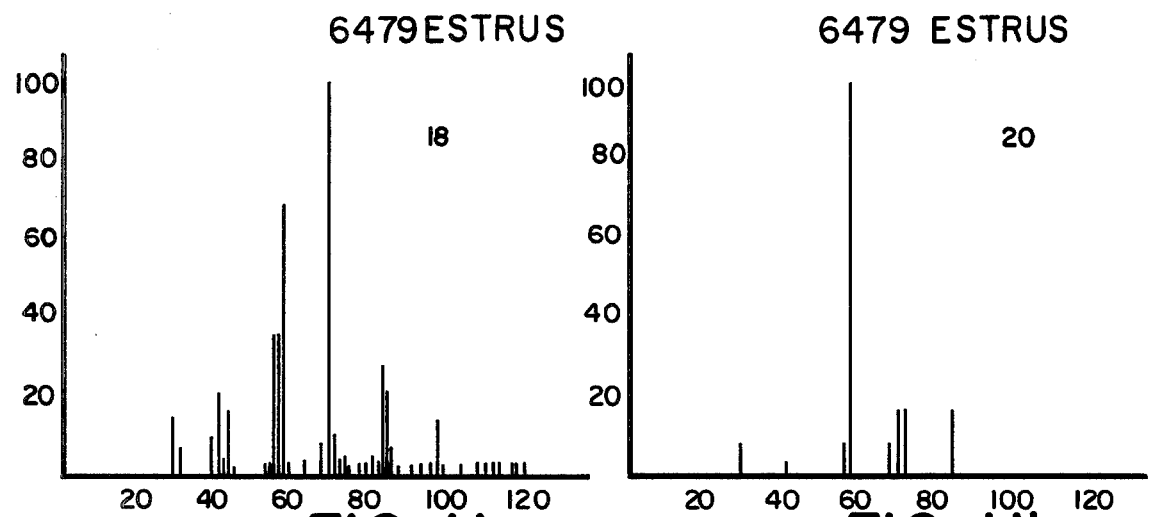
Figures 11C, 11D:
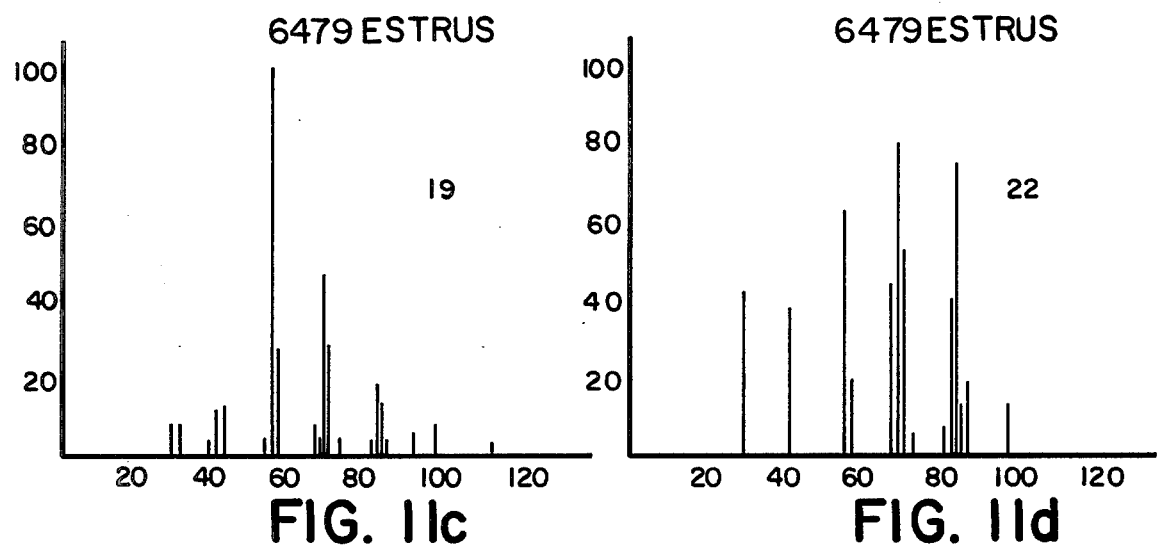
Figure 11E:
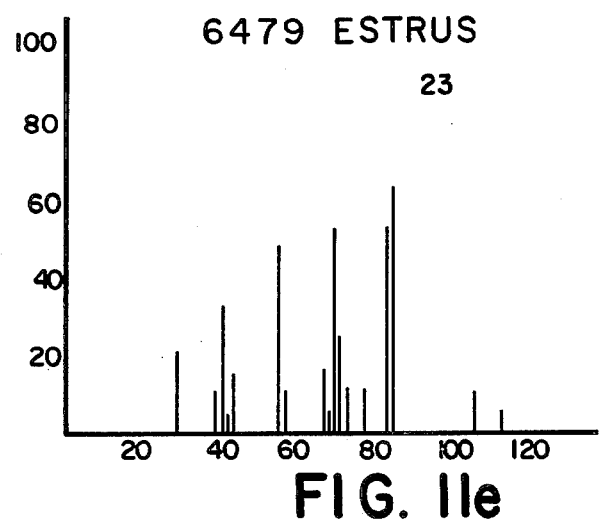
Figure 12A:
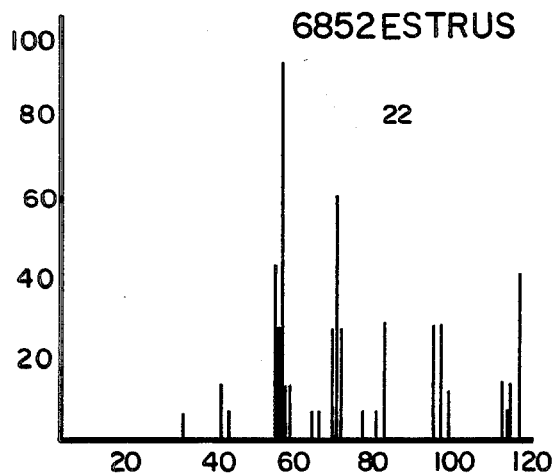
Figure 12B:
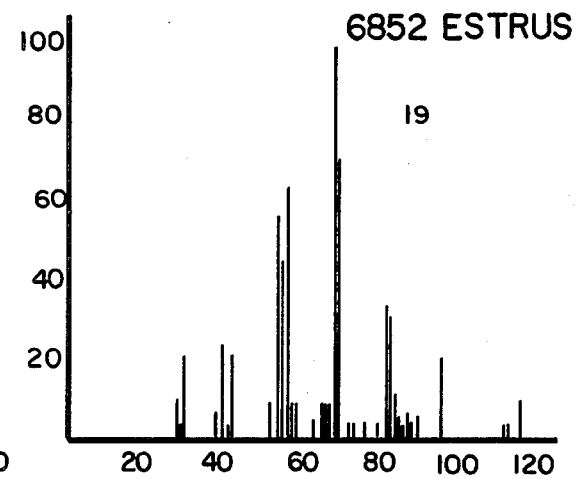
Figure 12C:
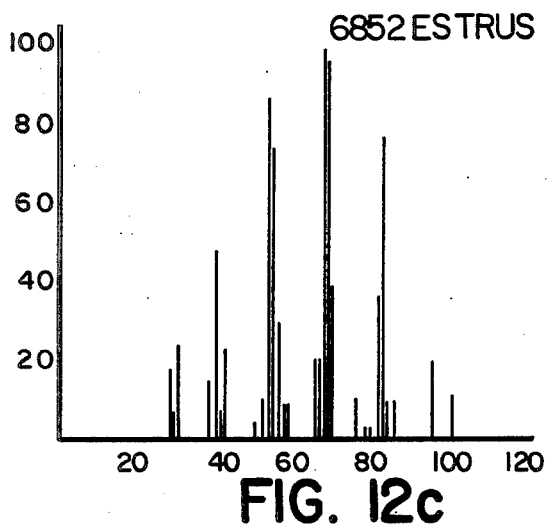
Figure 12D:
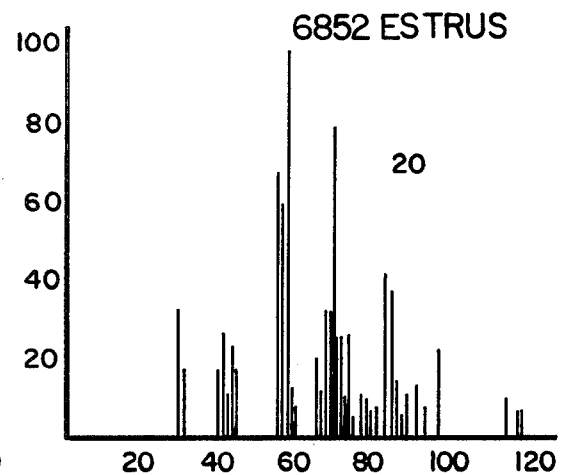
Figure 12E:
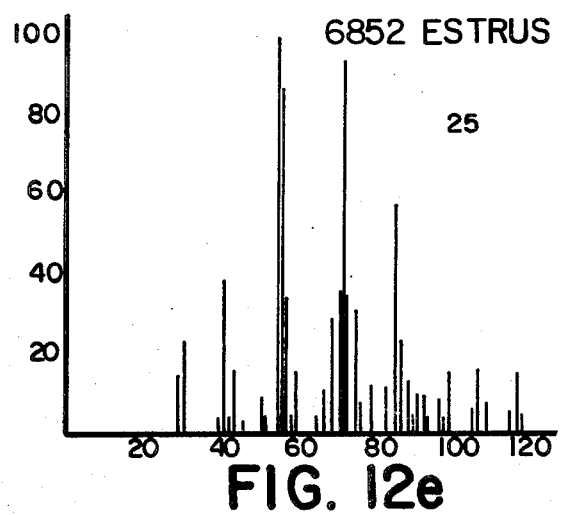
Figure 14A:
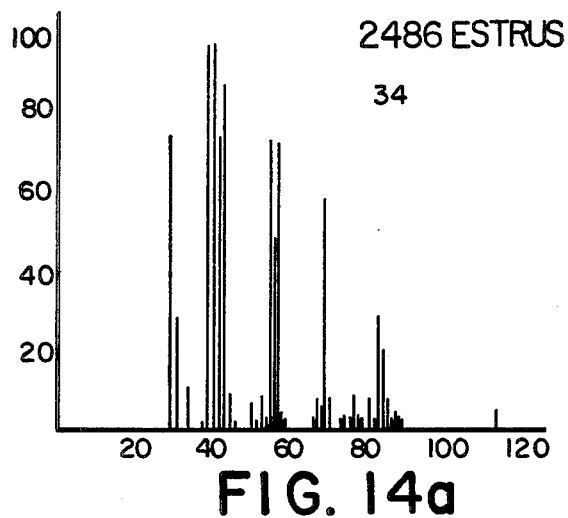
Figure 14B:
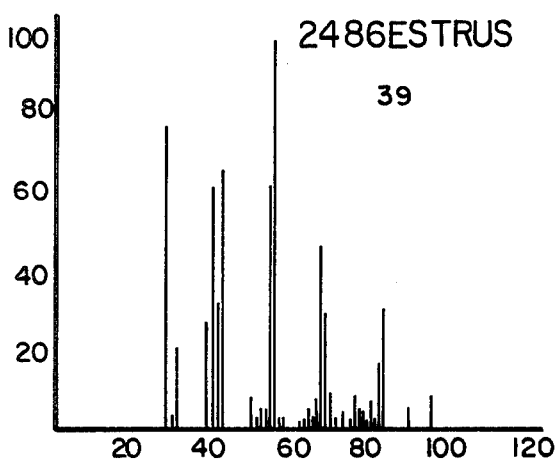
Figure 14C:
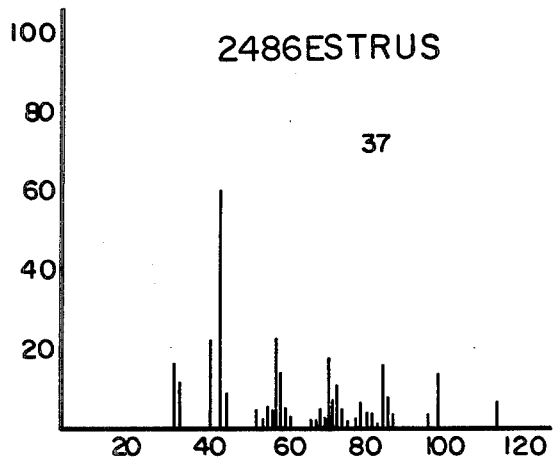
Figure 14D:
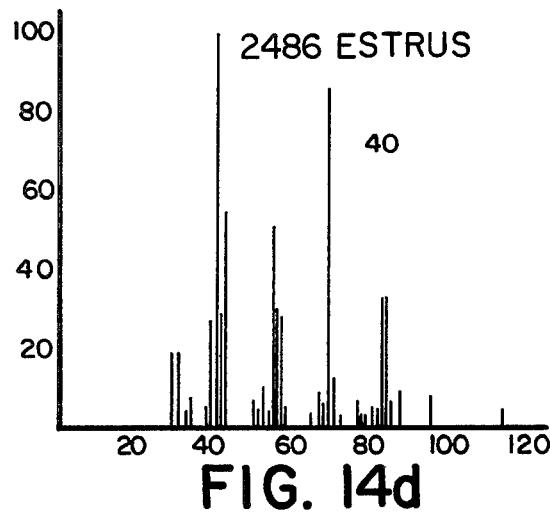
Figure 14E:
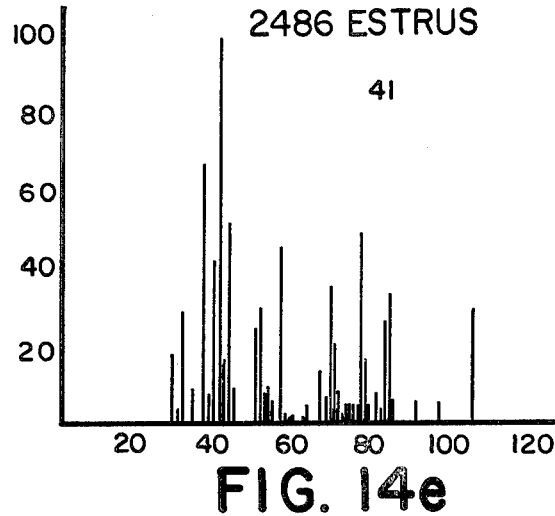

As may be seen from FIGS. 1-7 there is a great deal of inter-cow variation in the amount of compounds collected. Greater amounts of constituents however, are seen in the E samples and this difference approached significance even in the small number of animals investigated here. N=7; peak area E=325.3±54.2 (SEM); peak area NE=109.9±18.2 (SEM); t=2.41; $0.05 \leq p \leq 0.1$; peak areas in mm². The structual nature of the constituents eluting in the area of interest have been examined by combined gas chromatography/mass spectrometry (GC/MS) and the normalized mass spectra from each of the estrous samples are shown in FIG. 8-14. The number found on each of the spectra corresponds to its scan number which is indicated on the corresponding chromatogaphic profiles seen in FIGS. 1-7. The salient features of the mass spectra eluting in this region of the chromatogram are intense and characteristic ions at m/z 31,41,43,55,56,57,69,70,83,84, and 97. In addition to these ions, ions characteristic of benzaldehyde (i.e., m/z 77,105,106) are seen in several of the spectra: cow 6812 #22; cow 2486 #41; cow 6479 #23; cow 2443 #29. This compound was found to elute in these animals in the region of the chromatograms shown in FIGS. 1-7.

The ethyl ester index of benzaldehyde is 8.95 consequently, from this and comparison of the chromatographic profiles in FIGS. 1-7 with injection of the ethyl ester (EE) mixture done under identical chromatographic conditions, the three peaks of interest have EE indices (EEI) centered at 8.15, 8.5 and 8.90—see FIGS. 1-7.

From both the gas chromatographic and GC/MS data, the peaks eluting in the area of interest do not appear to be homogenous and this may account for differences seen in the relative ratios of the major ions. In addition, spectra from animals 2486 and 2406 were obtained on a different ion source than those from the remaining 5 animals.

Four spectra taken in the area of interest from cow 6806 (see FIG. 9) were normalized and searched through a computerized library of 31,600 mass spectra at the MIT Mass Spectrometry Laboratory. Results for three of the spectra are shown in FIGS. 16-18. Seven and eight carbon alcohols appear to have high similarity to the unknowns, but the seven carbon alcohols can be eliminated since their EEI's are to low to be eluting in the area of interest. The hydrocarbons listed in FIGS. 16-18 as well as the $C_{11}$ and $C_{12}$ alcohols and aldehydes do not appear to be correct since their EEI's are undoubtably too high to be eluting in the area of interest.

Figure 15A:
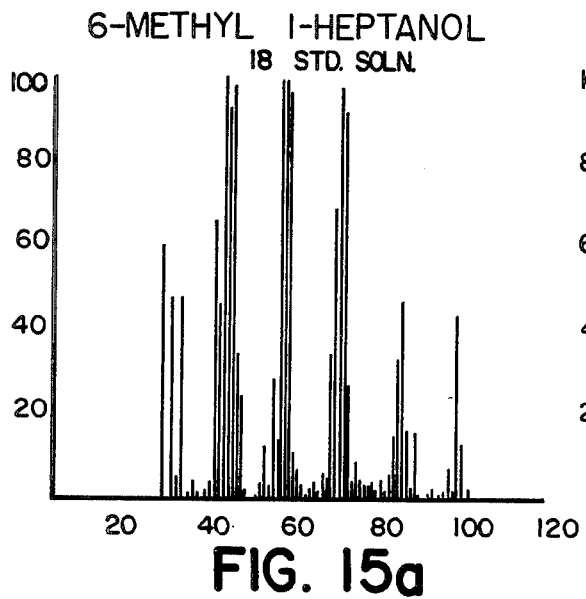
FIG. 15 are mass spectra generated using 6-methyl-1-heptanol obtained from a commercial source (Aldrich)
Figure 15B:
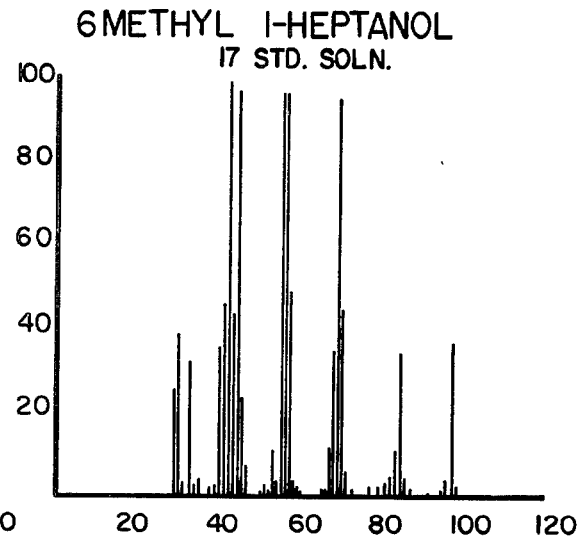
Figure 15C:
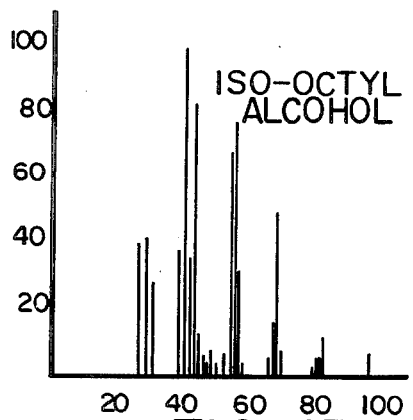
Figure 15D:
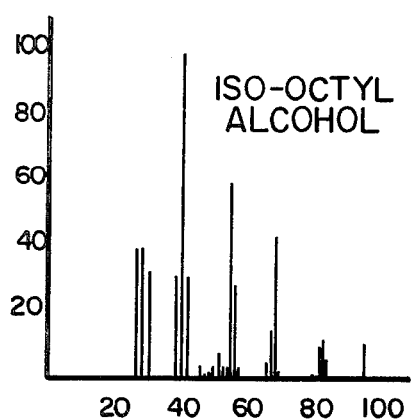
Figure 15E:
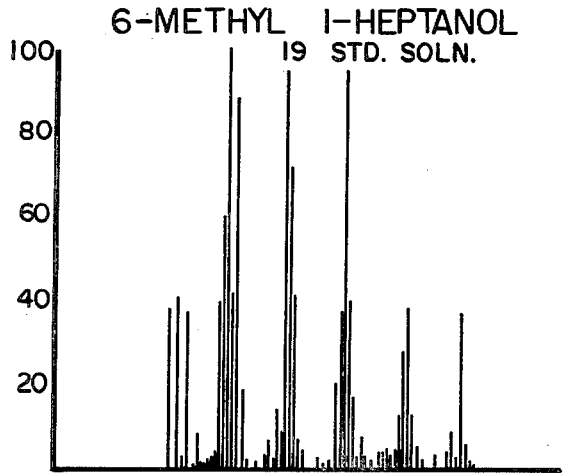

Authentic 6-methyl-1-heptanol was obtained from a commercial source (Aldrich) and used to obtain the spectra seen in FIG. 15. These spectra show that the m/z 41 and 43 ions are the most intense. The EEI of 6-methyl-1-heptanol as measured on a 100 ft Carobwax 20M capillary column was 8.85. The spectra from the cows obtained in the region of the chromatogram whose retention time corresponds most closely to 6-methy-1-hexanol are marked with an asterisk(*) (see FIGS. 8-11). Spectra from cows 6806 and 2486 have the greatest similarity to the authentic spectrum shown in FIGS. 9 and 14. Those from 6479, 6852, 6812, 2442 have m/z 69 as their largest ion, suggesting that another compound which has an intense ion at this m/z value is co-eluting with 6-methyl-1-heptanol here. This compound could be present in small amounts and merely contribute to the m/z 69 ion.

The spectra from the compound eluting at EEI 8.15 appears to be similar to 6-methyl-1-heptanol and is believed to be isomeric with it. The 5- or 4-methyl-1-heptanols are the probable isomers, however, authentic samples or literature data have yet to confirm this data.

As may be seen in FIGS. 1-7, 5 of the 7 non-estrous samples had compounds eluting in the area of interest. The remaining two animals showed no constituents eluting in this area of interest (see FIGS. 3 and 4) and mass spectra taken in the region of interest showed only background. Representative mass spectra were also obtained for these non-estrous samples. Only two spectra from cow 6806 appear similar to compounds seen in the estrous samples. Spectrum 27 from cow 6806 was determined to be that of n-pentadecane, which has a molecular ion at m/z 212 and an EEI of 8.7.

The standard solution of 6-methyl-1-heptanol was used to impregnate 5 pairs of clean tampons with varying amounts of this compound. Volatiles from these tampons were then collected and extracted as described above. These data suggest that 1–5 micrograms were present in the estrous tampons and that far less than 0.1 micrograms were present in non-estrous samples. Accordingly, a quantitative determination of 6-methyl-1-heptanol in amounts of about 0.1 to 1.6, preferably 0.16 to 0.83 microgram per gram of collected secretion is indicative of estrus at least when the collected sample weights are within the standard deviation for the sample collection procedure. Lower concentrations do not indicate estrus. Alternatively, absolute amounts of 6-methyl-1-heptanol collected using a standard collection method, such as the one described herein, may be used as an absolute indicator of estrus.

From the foregoing, one of ordinary skill in the art will recognize that headspace collection and concentration procedures are presently preferred for detecting and determining the amount and concentration of indicator compounds in accordance with the present invention. To date, extraction methods have not been successful in distinguishing between estrous and non-estrous cycles. As seen from the above, a simple diagnostic technique is provided having great practical utility to the management of diary and beef cattle.

Further information relating to the present invention and to the general field of this invention is set forth in the following description, which constitutes the pertinent portion of a not-yet-published grant application pertaining to the subject matter of this application:

"A. Objectives

"Studies conducted within the past 10 years have documented the extent to which odors affect the reproductive biology of mammals (Melrose et al., 1971; Preti et al., 1977; Goodwin et al., 1979; Epple, 1982). Only a small number of investigations have sought to document and define the nature and extent to which odors are used by cattle in their reproductive behavior (Kiddy et al., 1978; Paleologou, 1977; Price and Manning, 1978). Analyses of the odorous metablites produced by humans and non-human mammals have made us aware that these volatile (odorous) metabolites may provide important insight into body functions, such as indicating the time of estrus, pregnancy and various pathologies.

"Consequently, we propose to examine the volatile metabolites produced in the vaginal fluids and milk of cows in conjunction with measuring the plasma profiles of 17-estradiol, progesterone, testosterone and leutenizing hormone. The proposed study will be the first interdisciplinary, in-depth examination of volatile metabolites from cows and how they relate to reproductive hormonal levels in these animals.

"The specific aims of this study projected over a 2 year period are as follows:

"1. To determine the nature and abundance of volatile metabolites in the vaginal secretions and milk from estrous and non-estrous cows so as to investigate qualitative and/or quantitative differences in the volatiles across the estrous cycle;

"2. To determine the relationship between the production of volatiles characteristic of estrus and plasma levels of 17-estradiol, progesterone, testosterone and leutinizing hormone.

"Objective #1 will be accomplished using 20 cows across 3 estrous cycles/cow. Objective #2 will be accomplished using 12 cows across 3 estrous cycles/cow. Each objective will employ a separate group of animals. The amount of data generated by this number of animals will be large and preclude the use of a larger n if the objectives are to be carried out.

"B. Procedures

"General

"The proposed research will bring together the expertise of an organic-analytical chemist trained in mass spectrometery (Dr. Preti) and that of an endocrinologist who has extensive experience in radioimmunoassay procedures (Dr. Katz) with Dr. Harold Hawk and his staff who will provide the samples of vaginal fluids, milk and blood.

"1. Animals

"Healthy cows (Holsteins) from the dairy females in the Beltsville herd will be used as subjects. They will be at least 40 days postpartum and undergoing normal, regular estrous cycles.

"2. Collection of Vaginal Secretions and Milk

"(a) Commercially available tampons (Tampax) will be employed for collection of vaginal fluids. These were pre-cleaned in our laboratory using previously documented techniques (Preti and Huggins, 1975; Huggins and Preti, 1976). After extraction, drying and weighing, the tampons are returned to their original holders and stored in clean glass bottles. Jars for placing the tampons in after secretion collection as well as jars for milk collections were all cleaned in our laboratories. The cleaning procedures were similar to those used for cleaning glassware employed in the analyses of returned lunar samples (Preti et al., 1971).

"(b) Vaginal fluids will be collected on tampons inserted against the anterior vagina using a glass speculum. Tampons will be left in place for 1 hr.

"(c) Milk samples will be obtained from mixed milk during the normal milking process. Thirty ml samples of milk will be collected. Samples of body fluids collected by USDA personnel will be frozen at −20° C. until shipment to the Monell Center. Samples will be packed in dry ice prior to shipment.

"Experimental Plan: First Year 9/1/82-8/31/83

"*During the first year* of the proposed study we will concentrate primarily on confirming and extending the results from our preliminary studies in order to establish the chemical structure of vaginal and milk metabolites which are characteristic of estrus. Cows will be observed on a daily basis to determine the day of standing estrus. Collections of vaginal fluids and milk will be made on this day. Vaginal secretion collection, as noted above will be done by leaving tampons in place for 1 hr. Collections of non-estrous vaginal fluid and milk samples will be made 8 to 10 days after estrus (Kiddy and Mitchell, 1981).

"In conjunction with these samples, blood samples will be obtained (with heparinized Vacutainer syringes) on the day of standing estrus, the day after standing estrus and the day the non-estrous samples are collected. The plasma samples will be assayed for levels of 17-estradiol, testosterone and progesterone to determine if these are (as described below) characteristic of a normal ovulatory cycle (Mann and Hafs, 1976).

"Results Expected

"The extensive organic-analytical investigations planned are expected to extend the results obtained in our preliminary studies by confirming the structure and amounts of the volatile alcohols present in bovine vaginal fluids which are indicative of estrus. We will also be able to determine whether or not milk contains volatiles of diagnostic value and the structures of these compounds. The large amount of instrumental facilities available to us as well as our past experience in the GC/MS analyses of body fluids will certainly aid in successful completion of these expectations.

"Experimental Plan: Second Year 9/1/83–8/31/84

"*During the second year* of the proposed study, we will establish the relationship between the production of volatiles characteristic of estrus and plasma hormonal profiles for LH, 17-estradiol ($E_1$), testosterone (T) and progesterone (P). In this part of the study, volatiles in either vaginal fluids or milk will be used depending on which yields the most definitive changes in volatiles during estrus: both will be monitored if necessary.

"Twelve cows will be used for this aspect of the study. Observations of the selected cows will be done to determine when each is in estrus: day $0_A$. Eighteen days following day $0_A$ we will begin daily blood collections for 7 consecutive days in conjunction with collections of body fluids for analysis of volatiles. Two samples each of body fluids and blood will be obtained on those days (in the 7 day interval) when observations indicate the cow is approaching estrus. This may allow for a better determination of when the LH peak occurred. Following this 7 day interval which should include the next day 0 (day $0_B$), collections of blood and vaginal fluids/milk will be done every third day until 18 days following day $0_B$ at which time collections will again be repeated for 7 consecutive days.

"The above collection procedure will be repeated to encompass 3 days of standing estrus (day $0_B$, $0_C$ and $0_D$) and 2 inter-estrous intervals (day $0_B$ day $0_C$ $0_D$). This collection procedure will yield approximately 29 samples of blood and vaginal fluids/milk per animal.

"Results Expected

"The results of Kiddy et al. (1978, 1981) as well as Ladewig and Hart (1981) suggest that the odors indicative of estrus are dependent on reproductive hormonal levels. In these studies, it was found that animals responded most positively to samples obtained on the day of estrus but response fell off rapidly as one moved away from this time. By monitoring both the important volatile constituents (identified in the first year) and the reproductive hormone levels we will be able to quantify the relationship (i.e., the statistical correlation) between levels of volatiles and levels of the four reproductive hormones being measured.

"Methodologies for Organic-Analytical/Hormonal Analyses

"*Organic-Analytical Analyses.* In addition to repeating collection of volatiles of Tenax, which showed the most definitive differences between the estrous and non-estrous vaginal samples, we also plan to examine each of the mucus and milk samples for volatile sulfur compounds (VSC). Vaginal mucus samples collected on Tampons will also be extracted as in our preliminary studies. VSC analyses and extractions will be repeated for the following reasons. Our instrumental sensitivity relative to when the preliminary study was run has increased approximately 10 x due to addition of an amplifier for the Flame Photometric Detector. The GC/MS data system which will be used for the proposed study, and which we are currently evaluating (see Facilities and Equipment) is 100 to 1000 x more sensitive than the GC/MS we employed in our preliminary studies. Consequently, we expect to be able to examine the proposed samples at greater sensitivity and thereby obtain more qualitative and quantitative data from them. In addition, we will be able to run larger numbers of samples than before and more efficiently analyze the resulting data because of the data system and its software options. These were not previously available.

"We anticipate using the vaginal fluid and milk samples collected from 20 cows (3 estrous cycles each) to be analyzed first for VSC, followed by collection of headspace on Tenax and then, in the case of tampons, extraction of the samples. This will help confirm the preliminary results and further aid in the structure elucidation of the compounds of interest (see Current Research, below) as well as providing an in depth study of milk volatiles. Samples obtained from the remaining (8) cows will be used to provide the necessary material for further structure elucidation of the vaginal volatiles having ethyl ester units 8.15 to 8.90 (see FIGS. 3–6 in Appendix 1) and any other compound(s) which appears to be important for estrous detection. This may require divergence from a set analytical scheme and necessitate combining estrous samples to provide sufficient amounts of material to allow for preparative collection of microgram amounts of the desired compounds. As noted in the Facilities and Equipment section, we have complete access to high resolution mass spectrometry and nuclear magnetic resonance facilities to facilitate structure elucidation. Regardless of whether estrous samples are combined or run individually the exact same procedures will be carried out using the corresponding non-estrous samples.

"*Internal Standardization.* In the preliminary study, heptanoic acid was employed as the internal standard but only for extracts. No internal standardization was used during headspace collections.

"The proposed study will employ 1-dodecanol as an internal standard during both collection of volatiles and extractions. We have recently determined that the volatility and polarity of 1-dodecanol more closely approximates 6-methyl-1-heptanol (and probably other alcohols in the estrous secretions) than heptanoic acid. Twenty five (25) micrograms of 1-dodecanol will be added to each tampon and 5 cc milk sample prior to headspace collection. We are currently performing model experiments to determine how much 1-dodecanol is collected during the 90 min headspace collections. This determination is necessary so that an aliquot of 1-dodecanol can be added to the tampons prior to extraction to bring the amount back to 25 g.

"The use of an internal standard will allow the amount of volatile metabolites recovered from the headspace collections and extractions to be calculated.

Peak areas of chromatographic peaks will be converted to microgram amounts for presentation.

"a. *Analysis for Volatile Sulfur Compounds.* Volatile sulfur compounds (VSC) such as hydrogen sulfide ($H_2S$), methyl mercaptan ($CH_3SH$), dimethyl sulfide (DMS, $CH_3SCH_3$) are strong olfactory stimulants even at low parts per billion concentration (Tonzetich and Ng, 1976; Ohloff, 1978). Consequently, milk and vaginal fluids will be analyzed on our gas chromatograph which is equipped with a Flame Photometric Detector (FPD) and specifically modified to analyze for VSC at the ppb level. This type of analytical system has been described previously in the literature (Tonzetich and Ng, 1976) and has been adapted by us to sample and analyze for VSC from a variety of closed systems. The instrumentation consists of a Perkin-Elmer 3920 fitted with both a Teflon injector, column and transfer valve to prevent loss of VSC due to absorption that can occur on glass or metal surfaces.

"The tampon will first be weighed to record the secretion weight and then placed in 100 cc round-bottom flask and equilibrated for 15 min at 39° C. prior to headspace sampling. Five cc of milk will be similarly equilibrated in a 25 cc, 2 neck flask. One neck of the flask is fitted with a $6'' \times \frac{1}{8}''$ stainless steel tube filled with 100 mg Tenax (an organic polymer—see below) through whch air is drawn. The second neck is connected to the chromatograph's injection system via an adapter and a Teflon line. Aliquots of headspace are aspirated from the flask into a 10 ml sample loop component of a pre-column, air-actuated, automatic injection system (Tonzetich and Ng, 1976). The contents of the loop will be transferred via a 6-port valve onto a 36 ft.$\times \frac{1}{8}$ in. O.D. fluorinated ethylene propylene Teflon column packed with 5% polyphenyl ether and 0.5% $H_3PO_4$ on a 40–60 mesh chromsorb T and chromatographed using the following program: 70°-8 min., 70°–166° at 32°/min., 166°-16 min. "Zero air" at 25 ml/min flow rate will be used as the carrier gas. The output of the FPD is displayed on a dual pen recorder.

"Concentrations of the sulfur components will be calculated from standard graphs derived from analyses of known concentrations of compounds. Individual calibration curves are prepared from all volatile sulfur compounds by diluting with $N_2$ the corresponding permeation tube standards (Analytical Instrument Development, Inc., West Chester, PA) to the desired concentrations (Tonzetich and Ng, 1976).

"The column employed for separation as well as the temperature program protocol employed during analysis are designed to reveal the presence of higher molecular weight volatile sulfur compounds which elute after $H_2S$, $CH_3SH$ and $(CH_3)_2S$.

"b. Collection, Concentration and Analysis of Milk and Tampon Headspace Volatiles Using Tenax "After VSC measurement, 25 g of 1-dodecanol (internal standard) will be added to the milk/tampon. The flask holding the milk or tampon will then be moved to a second isothermal bath and re-equilibrated to 39°±1° C. With each sample, the round-bottom flask will be sealed with Teflon joints through which passes a nitrogen line and clean Tenax tube. Using a nitrogen flow rate of 120 ml/min (Kostelc et al., 1980). Volatiles will be swept out of the flask and through the $6'' \times \frac{1}{8}''$ (O.D.) stainless steel tube filled with 100 mg of Tenax (a 2,6-diphenyl-p-phenylene oxide polymer, Applied Science Labs., State College, PA). This polymer adsorbs organic compounds but retains little water and effectively concentrates organic compounds from aqueous sources (see Sastry et al., 1980; Kostelc et al., 1980; and Zlatkis et al., 1981, reviews the use of this technique).

"One 90 minute collection will be made from each of the milk or vaginal headspace samples. These samples will be stored in the Tenax tubes at −60° C. until needed for analysis by combined gas chromatography/mass spectrometry.

"c. Extraction of Vaginal Organic Compounds from Tampons.

"A second aliquot of 1-dodecanol will be applied along the length of the tampon (as noted above) at this time to re-establish its level at 25 g. Organic materials are then extracted using 150 ml of dichloromethane ($CH_2Cl_2$/methanol ($CH_3OH$); 85/15; for 24 hr in a Soxhlet apparatus.

"Each extract will be concentrated to 200–300 l by rotary evaporation at room temperature. Ten l of each extract will be injected onto a Carbowax column for analysis while 60 l of each extract will be used to form trimethylsily ethers and esters. These derivatives will be formed by placing 60 l in a cone-shaped, 200 ul "Reacta-Vial" (Pierce Chemical Company, Rockville, IL) evaporating to dryness using a water aspirator and immediately adding 40 l BSTFA and 10 TMCS. This reaction mixture was allowed to stand at 60° C. for 90 min prior to gas chromatographic analysis.

"d. GC and GC/MS Analysis of Headspace Collections and Extracts

"Our current GC/MS system consists of a Perkin-Elmer 990 GC interfaced to a Hitachi RMU-6L mass spectrometer via a Watson-Biemann separator (Watson and Biemann, 1965). We are currently seeking to purchase a state-of-the-art GC/MS/data system which will also enable us also to interface our RMU-6L with the data system. Identification of all compounds will be confirmed by comparison of mass spectra and chromatographic retention times with those from either commercially available or synthetically produced samples.

"In addition other spectroscopic techniques (nuclear magnetic resonance or infrared) will be used as needed. Relative retention times on Carbowax will be obtained by coinjection of headspace mixtures, extracts or authentic samples with a series of $C_2$–$C_{18}$ fatty acid ethyl esters to obtain their "ethyl ester index" (Van der Dool and Katz, 1963). A homologus series of $C_9$–$C_{36}$ hydrocarbons will be employed to obtain relative retention times of silylated derivatives. In the preliminary study the headspace samples and extracts were analyzed on packed columns. However, we have been adapting these analyses to a $100' \times 0.04''$ Carbowax 20M columns using test mixtures of 5-methyl-1-hexanol, 6-methyl-1-heptanol (isooctylalchol) and benzaldehyde. The columns are made in our laboratory and are wall coated. They have from 1000–2000 plates per meter and yield excellent separations of compounds eluting in the relative retention time "window" of interest: EEI 8.0 to 9.0. Since actual samples have yet to be run on these columns we plan to run several initial samples on both the packed and capillary columns before initiating the actual experimental plan. Separations with test mixtures yield maximum separations using the following conditions: isothermal 115° C. for 25 minutes then 2°/min to 200° C. using 10 ml/min flow of He. The packed column is a $12' \times 0.04''$ (i.d.) glass 10% Carbowax 20M column with a 40 ml/min He carrier gas flow. The temperature program protocol used will be 50° C. for 8 min.; 50°–230° 4°/min., 230° for 30 min.

"(i) Headspace Samples

"Organic materials collected on the Tenax will be desorbed from the polymer and onto the front 6-8 in. of the packed Carbowax column which is cooled using crushed dry ice. The Tenax will be rapidly heated to 240° C. for 15 min while its contents are swept by means of the carrier gas (He) onto the column. After desorption is complete, the dry ice will be removed, the Tenax tube removed from the GC injector, the flow rate resumed through the GC column and the components separated on the column following the programmed temperature conditions cited above. When the capillary column is used the entire oven is cooled to −40° using dry ice before desorption of volatiles from Tenax.

"(ii) Extracts

"The Carbowax columns described above will be employed to separate and analyze constituents found in either 10 l (for packed column) or 1 l (for capillary column) of extract using the following temperature programs: packed column, 70° for 4 min.; 70°–230° 3°/min.; 230° for 30 min., capillary column, 90° (8 min)-200° C., at 2°/min. Silylated derivatives were separated and analyzed using a 12'×0.04" (i.d.), glass, 3% SE-30 column with a 40 ml/min He carrier gas flow and the following temperature program: 70° for 4 min.; 70–310 4°/min.; 310° for 30 min. Separation of the silylated esters and ethers are being adapted for use on a 100'×0.02" column coated with SE-30.

"Plasma Hormone Assays

"Whenever blood is sampled, it will be withdrawn into heparanized containers. The separated plasma will be kept frozen at −60° C. until it is assayed. Determinations of plasma levels of sex steroids (E,P and T) and LH will be performed in the Monell Center's endocrine laboratory under Dr. Katz's direction. RIA techniques developed in our laboratory (Katz et al., 1982) will be employed for steroid analyses and a commercial kit (Amersham's) will be used for LH assays.

"C. Justification/Significance

"An optimal test for estrus should be simple, relatively inexpensive and able to be performed routinely. Such a method is still being sought (Ladewig and Hart, 1981). It is currently estimated that from 40-60% of all estrus are missed which is a major cause of reproductive inefficiency in cattle bred by artificial insemination (AI) (Kiddy, 1978). Each missed estrus delays insemination by 3 weeks and results in loss of milk production in dairy cattle and loss of offspring in both dairy and beef cattle. Detection of estrus has become more acute with increased dairy herd size, escalating labor costs, and with use of loose housing systems for dairy cattle and use of AI in beef herds. Identification of one or more metabolites in a readily accessible body fluid (vaginal secretions or milk) would be an important step in eliminating this problem.

"The types of compounds identified in our preliminary studies are simple in structure and may lend themselves to easy detection. Consequently, once the compounds are definitively known and the temporal relationship between these compounds and estrus/ovulation is established it is feasible to envision one or more of these compounds being used in a simple test to provide the herdsman with a reliable indication that estrous is occurring or about to occur.

This study will also establish the normal profile of volatile organic metabolites in bovine vaginal fluids and milk; information which is not currently known. The information content of these volatiles is quite extensive if analogies to humans and other mammals can be drawn (Preti et al., 1977; Sastry et al., 1980; Signoret, 1976; Epple, 1982). Consequently, once the levels of normal metabolaites in healthy cows is known, it will be possible to apply the same organic-analytic techniques to the early diagnosis of pregnancy and reproductive pathologies.

"The use of high sensitivity organic-analytical instrumentation in the profiling of volatiles metabolites from human body fluids is becoming an exciting frontier in medical diagnosis (Sastry et al., 1980; Zlatkis, 1981). Our previous studies employing GC and GC/MS techniques in the analysis of human body fluids have identified several metabolites in both vaginal fluids and the oral cavity which are indicative of the time of ovulation (Huggins and Preti, 1976; Preti and Huggins, 1978; Tonzetich et al., 1978; Preti et al., 1980). In addition to our own studies there is a growing body of literature which shows that GC/MS is creating new approaches in the diagnosis, detection and monitoring of normal and pathologic states (Sastry et al., 1980; Zlatkis, 1981). These studies in conjunction with the demonstration that odors characteristic of estrous are present in bovine body fluids (Kiddy et al., 1978, 1981; Ladewig and Hart, 1981), provide substantial rationale for the application of organic-analytical techniques to the analysis of these fluids. In addition, it will be necessary to define the temporal relationship between the production of volatiles (odors) characteristic of ovulation and plasma levels of sex steroids and LH if the results of the study are to have practical application in aidding artificial insemination. The clearly discernable differences found between estrous and non-estrous volatiles in our preliminary studies suggest that the instrumental techniques which shall be used in the proposed study will lead to the definitive identification of one or more compounds which are indicative of estrus in bovine.

"D. Literature Review

"The importance of estrous detection in bovine, in which reproduction is primarily based on AI, is well established (Manns and Hafs, 1976). This has led to a variety of attempts to establish a simple method to determine this important time. These have included the amount of movement displayed during the estrous cycle (as measured by a pedometer) (Kiddy, 1978) and measurement of electrical resistance of vaginal mucus (Gartland et al., 1976).

"Sambras and Waring (1975) documented the ability of sexual experienced bulls to discriminate estrous females from non-estrous ones on the basis of urinary odors. In addition, Paleologou (1977) found that vaginal mucus from estrous cows would stimulate bulls to mount dummies used for semen collection. Mucus from non-estrous cows had no effect. Studies such as these suggest that bulls may base part of their discrimination between estrous and non-estrous cows on odors found in the genital region of female bovine. Consequently, while the role of behaviorally important odors from estrous cows in attracting bulls has not been definitely established, there is evidence for the existence of such odors.

"An effort to document the types of compounds present in cow urine which might change during the extrous cycle was reported by Price and Manning (1978). Using a headspace concentration technique in combination with GC/MS, they examined concentration changes in approximately 30 volatile compounds on a daily basis across 3 estrous cycles from 1 non-lactating cow. No reproducible changes were seen in the concentration of these volatiles, even though the cow displayed good estrus behavior.

"Studies by Kiddy et al. (1978, 1981) employing trained dogs, show that these animals can differentiate odors from a variety of cow body fluids (blood, milk, urine, vaginal secretions) obtained from estrous and non-estrous cows. Hence, a quantitative and/or qualitative change in the volatiles from readily available sources are characteristic of estrus. Another recent investigation by Ladewig and Hart (1981) found that rats could be trained to detect estrous-related odors in cow urine. It is not surprising that the rats used in this study were able to find a difference in the urinary odor while instrumental methods were not, since mammalian olfactory abilities often exceed the instrumental sensitivity of a GC/MS used in the normal scanning mode.

"Each of these studies demonstrate that there is a characteristic change in excreted metabolites due to a change in hormonal state. However, it is not known if the dogs and rats are employing the same odors that bulls employ.

"E. Current Research

"The studies employing sensitive mammalian olfaction to document the presence of estrous related odors suggested to us that these compounds could be isolated and identified by organic-analytic techniques particularly if vaginal fluids and/or milk were employed. In humans, these fluids have been shown to be less complex in terms of volatiles than urine (Sastry et al., 1980; Preti and Huggins, 1978).

"In collaboration with Drs. Charles Kiddy and Harold Hawk of the Reproduction Laboratory, Animal Science Institute, USDA, Beltsville, Md. we began to test this possibility. They provided samples of vaginal fluids and milk to us for analyses. The procedures we employed in our preliminary study are silimar to those for the proposed research and are discussed in the Procedures. The results obtained are summarized below.

"1. Vaginal Secretions

"A total of 18 estrous (E) and 18 non-estrous (NE) samples of vaginal fluids collected on tampons were received in our laboratories. These were used in one or more of the analytical procedures described below. Six paired E and NE samples were used only in the extraction protocol. Five paired E and NE samples were analyzed for volatile sulfur compounds and then by collection of the volatiles in their headspace on Tenax, 3 paired E and NE samples had the volatiles in their headspace collected on Tenax (a phenylene oxide porous polymer) followed by analysis using the extraction protocol, and 1 pair was analyzed only by collection of headspace volatiles on Tenax.

"Regardless of the sequence of analytical procedures performed on tampons, the profiles of constituents obtained by extraction or Tenax collection were similar. Consequently, the results obtained from all extracts will be discussed together as will the results from Tenax collections and VSC analyses.

"a. Secretion Weight

"Each of the tampons were left in the vagina for 1 hr. A paired t-test was used to give a measure of the difference in secretion weight during the 2 stages of the estrous cycle: secretion weight during estrous=6.028 gm±3.004 (S.D.); secretion weight during non-estrous=0.899 gm±0.747 (S.D.); t=7.485, p 0.001. The range seen in secretion weight was 0.489 gm to 11.253 gm for estrous samples and 0.001 gm to 2.083 gm for non-estrous samples.

"b. Volatile Sulfur Compounds

"Analysis for volatile sulfur compounds (VSC) in the headspace from tampons containing the secretions of 5 E and 5 NE cows were performed. This showed that traces (0.1–0.4 ng) of either $H_2S$, $CH_3SH$ or $(CH_3)_2S$ were present in 10 cc of headspace from 3 E samples and 2 NE samples. No sulfur compounds were found in the headspace of the remaining 3 samples. However, since the procedure for measuring VSC is relatively simple and our instrumental sensitivity has been increased since the above measurements were made, we have left this part of the protocol in the current proposal.

"c. Extractions

"i. Carbowax Chromatograms. Organic constituents extracted from the tampons were analyzed directly on a packed column with Carbowax liquid phase as in previous studies (Huggins and Preti, 1976; Preti et al., 1979). Table 1* shows the compounds found in the extracts with their retention times relative to a series of ethyl esters (van den Dool and Kratz, 1963). These compounds were seen in one or more E and NE cows with considerable individual differences. The differences in individual chromatographic profiles may be seen in FIGS. 1* and 2*. Heptanoic acid is the internal standard (INT STD) and may be used as a reference point since it elutes at an ethyl ester index of 12.78 (see Table 1*). Several other representative compounds including those found in Table 2 are also indicated in the above figures. No qualitative differences of a consistent nature could be found in constituents from the 2 different states of estrus. However, quantitative differences were seen in a number of compounds which were consistently present in the analyzed samples. These are shown in Table 2*.

*See Appendix I.

"As may be seen from Table 2*, there is a trend for non-estrous samples to contain a larger concentration of organic constituents than estrous samples. For the acidic constituents this difference is significant at the 0.05 level. However, even for acetic acid there is considerable individual variation as may be seen in Table 3* where concentrations of acetic acid in individual animals are listed.

"ii. Trimethylsilyl derivatives. A portion of each of the extracted samples was reacted with BSTFA and TMCS as described below. There was little consistency in the differences seen between E and NE samples in the resulting chromatograms. Some E samples were found to contain both greater numbers of constituents or more of individual constituents than their NE counterparts. While in other paired samples, the NE sample had either greater numbers of compounds or more of individual constituents.

"d. Headspace Collections on Tenax

"Volatiles present in the headspace above nine paired E and NE samples were individually collected on Tenax. Two, 2 hr collections were done in each case. The volatiles present in the second 2 hr sample were qualitatively identical to those in the first 2 hr collection; however, the first collections always contained larger amounts of constituents. The data from two of these animals is excluded from the discussions below for the following reasons: one animal was used in the initial experiment using Tenax when procedures were still being developed; and one animal showed a series of constituents never again seen in another animal. Consequently, this animal may have had some sort of vaginal anomaly which caused the appearance of these constituents.

"The compounds seen in the 7 remaining samples are listed in Table 4*. In these animals, a distinct difference was seen in the volatiles from the E and NE samples. The profiles of constituents collected during the first 2 hr collection from these samples may be seen in FIGS. 3–6*. The estrous samples show a series of peaks eluting between the times 25–35 min in cows 6812, 2443, 6806, 6852 and 6479 as well as times 30–40 min in cows 2406 and 2486. The retention times of the peaks in the latter 2 samples is the same as that in remaining 5.

"As may be seen from FIGS. 3–6*, there is a great deal of inter-cow variation in the amount of compounds eluting in the time windows cited above. However, greater amounts of volatiles are found in the E samples and this difference approaches significance even in the small number of animals investigated here: N=7, peak area E=325.3±54.2 (SEM); peak area NE=109.9±18.2 (SEM); t=2.41; 0 005 p 0.1 (peak areas in $mm^2$). The structural nature of the constituents eluting in the area of interest have been examined by combined GC/MS and the normalized mass spectra from each of the estrous samples are shown in FIGS. 7–13*. The number found on each of the spectra corresponds to its scan number which are indicated on the corresponding chromatographic profiles seen in FIGS. 3–6*. The salient features of the mass spectra eluting in this region of the chromatogram are intense and characteristic ions at m/z 31, 41, 43, 55, 56, 57, 69, 70, 83, 84 and 97. In addition to these ions, ions characteristic of benzaldehyde (i.e., m/z 77, 105, 106) are seen in several of the spectra: cow 6812 #22, cow 2486 #41, cow 6479 #23; cow 2443 #29. This compound was found to elute in these animals in the region of interest.

"The ethyl ester index of benzaldehyde is 8.95, consequently, from this and comparison of the chromatographic profiles in FIGS. 3–6* with injections of the ethyl ester (EE) mixture (see Section B, Procedures) done under identical chromatographic conditions, the three peaks of interest have EE indices (EEI) centered at approximately 8.15, 8.5 and 8.90—see FIGS. 3–6*.

"From both the gas chromatographic and GC/MS data, the peaks eluting in the area of interest do not appear to be homogenous. This may account for differences seen in the relative ratios of the major ions.

"Four spectra taken in the area of interest from cow 6806 (see FIG. 8*) were normalized and searched through a computerized library of 31,600 mass spectra at the MIT Mass Spectrometry Laboratory. Results for 3 of the spectra are shown in Tables 6–7* and suggest that seven and eight carbon alcohols appear to have high similarity to the unknowns. Isooctylalcohol (6-methyl-1-heptanol) is a strong possibility for one of the compounds. The hydrocarbons listed in Tables 5–7* as well as the $C_{11}$ and $C_{12}$ alcohols and aldehydes do not appear to be correct since their EEI's are too high to be eluting in the area of interest.

"Authentic 6-methyl-1-heptanol was obtained from a commercial source (Aldrich) and used to obtain the spectra seen in FIG. 14. These spectra show that the m/z 41 and 43 ions are the most intense. The EEI of 6-methyl-1-heptanol as measured on a 100 ft Carbowax 20M capillary column was 8.85. Spectra obtained from the chromatographic region of whose retention time corresponds most closely to 6-methyl-1-heptanol are marked with an asterisk (*) (see FIGS. 7–13*). Spectra from cows 6806 and 2486 have the greatest similarity to the authentic spectrum. Those from 6479, 6852, 6812, 2443 have m/z 69 as their largest ion, suggesting that another compound which has an intense ion at this m/z value is co-eluting with 6-methyl-1-heptanol here. This compound could be present in small amounts and merely contribute to the m/z 69 ion.

"The spectra from the compound eluting at EEI 8.15 appears to be similar to 6-methyl-1-heptanol and may well be isomeric with it. The 5- or 4-methyl-1-heptanol isomers are possibilities, however, no authentic samples or literature data are currently in hand to test this possibility.

"As may be seen in FIGS. 3–6*, 5 of the 7 non-estrous samples had compounds eluting in the area of interest. The remaining two animals showed no constituents eluting in this area (see FIGS. 4* and 5*) and mass spectra taken in this region showed only background. Representative mass spectra obtained in these samples are shown in FIGS. 15–19*. Only spectra 28 and perhaps 25 from cow 6806 (FIG. 16)* appear similar to those compounds found in the estrous samples. Spectrum 27* from cow 6806 is that of n-pentadecane which has a molecular ion at m/z 212 and an EEI of 8.7.

"A standard solution of 6-methyl-1-heptanol was used to impregnate 5 pairs of clean tampons with varying amounts of this compound. Volatiles from these tampons were then collected and extracted as with actual samples. These data suggest that 1–5 ug were present in the estrous tampons and that less than 1 ug were present in non-estrous samples.

"2. Milk

"a. Volatile Sulfur Compounds

"Only 3 pairs of estrous and non-estrous milk samples were analyzed due to our emphasis on the vaginal fluids. Each of these were examined for VSC content. Milk samples contained approximately 10× the level of VSC than vaginal fluids with 1–4 ng of individual compounds present. Two of the 3 animals had greater concentrations of VSC in the estrous sample.

"b. Headspace Collection on Tenax

"The differences seen in volatiles in the headspace above milk were more subtle than that found in vaginal fluids. In addition, the compounds which appear in the estrous samples but not in the non-estrous ones are low in concentration and definitive mass spectra could not be obtained with our current GC/MS system.

"3. Discussion of Results

Our preliminary study has been successful in identifying a group of compounds in the vaginal secretion of cows which may be indicative of estrus. Since the structural identity of these compounds are not known with certainty, except for the probable presence of isooctyalcohol, and only a small number of animals have been studied, these encouraging results need further investigation. Our proposed studies will enable us to extend these preliminary results by allowing us to definitively identify the group of vaginal fluid volatiles which are indicative of estrus, determine their concentration in vaginal fluids across the estrous cycle and determine their relationship to reproductive hormone levels. In addition, the new, state-of-the-art instrumentation to be employed will enable us to study the extracts for the compounds of interest which appeared to be below the instrumental sensitivity of our present system.

"The concentration of vaginal secretious constituents is low when compared to the amount of volatile organic constituents in human vaginal fluids (Preti et al., 1979; Preti and Huggins, 1975; Huggins and Preti, 1981). Alcohols are also present in human vaginal fluids, however, the chain length is larger: $C_{12}$ to $C_{18}$ (Huggins and Preti, 1981). These alcohols may arise from bacterial metabolism in humans, however; we presently cannot speculate as to the origin of the $C_8$ alcohols in the cow vaginal fluids."

I claim:

1. A method for determining when a cow is in estrus, comprising steps of:

monitoring said cow's vaginal secretions over time to detect an increase in the amount of at least one indicator compound contained in said secretions, said indicator compound being an eight carbon alcohol and having a gas chromatographic ethyl ester index of between about 8.1 and 8.9, said increase in the amount of said indicator compound being indicative of estrus.

2. The method of claim 1 wherein said alcohol is a methyl-1-heptanol.

3. The method of claim 2 wherein said heptanol is 6-methyl-1-heptanol.

4. The method of claim 1 wherein said alcohol is a 7-hydroxy-3-4 heptene.

5. The method of claim 4 wherein said alcohol is a 2-methyl-7-hydroxy-3-4-heptene.

6. The method of claim 1 wherein said amount increases to a concentration greater than about 0.1 micrograms per gram of secretion.

7. The method of claim 6 wherein said concentration increases to greater than about 0.16 micrograms per gram of secretion.

8. The method of claim 1 wherein said method further comprises collecting said secretion and analyzing the volatiles in the headspace of said secretion to determine said amount.

9. The method of claim 8 wherein the volatiles in said headspace are concentrated prior to analysis.

10. The method fo claim 1 wherein said compound elutes at an ethyl ester index of about 8.9.

11. The method of claim 1 wherein said compound wherein said compound elutes at an ethyl ester index of about 8.15.

12. The method of claim 1 wherein said compound elutes at an ethyl ester index of about 8.5.

13. A method for determining whether a given cow is in estrus, comprising:

determining the methyl-1-heptanol concentration in the vaginal secretions of said cow to ascertain whether said concentration is greater than about 0.1 microgram per gram of secretion, whereby a concentration greater than 0.1 microgram per gram of secretion is indicative of estrus.

14. The method of claim 13 wherein said concentration to be determined is greater than about 0.16 micrograms per gram of secretion.

15. The method of claim 14 wherein said concentration is less than 1.6 micrograms per gram of secretion.

16. The method of claim 13 wherein said methyl-1-heptanol is 6-methyl-1-heptanol.

* * * * *